(12) United States Patent
Kawrykow et al.

(10) Patent No.: US 11,931,602 B2
(45) Date of Patent: Mar. 19, 2024

(54) RADIATION THERAPY SYSTEMS AND METHODS

(71) Applicant: ViewRay Technologies, Inc., Oakwood Village, OH (US)

(72) Inventors: Iwan Kawrykow, Sofia (BG); Thomas Chmielewski, Aurora, OH (US); James F. Dempsey, Atherton, CA (US)

(73) Assignee: Viewray Technologies, Inc., Oakwood Village, OH (US)

( * ) Notice: Subject to any disclaimer, the term of this patent is extended or adjusted under 35 U.S.C. 154(b) by 287 days.

(21) Appl. No.: 17/227,155

(22) Filed: Apr. 9, 2021

(65) Prior Publication Data

US 2021/0220676 A1   Jul. 22, 2021

Related U.S. Application Data

(63) Continuation of application No. 15/840,941, filed on Dec. 13, 2017, now Pat. No. 11,000,706.
(Continued)

(51) Int. Cl.
*A61N 5/10* (2006.01)
*A61B 6/03* (2006.01)
(Continued)

(52) U.S. Cl.
CPC ............ *A61N 5/1081* (2013.01); *A61B 6/032* (2013.01); *A61N 5/1031* (2013.01);
(Continued)

(58) Field of Classification Search
CPC .............................. A61N 5/10; A61N 2005/10
See application file for complete search history.

(56) References Cited

U.S. PATENT DOCUMENTS

| 3,428,307 A | 2/1969 | Hunter |
| 4,019,059 A | 4/1977 | Brundin |

(Continued)

FOREIGN PATENT DOCUMENTS

| CN | 1612713 A | 5/2005 |
| CN | 1669599 A | 9/2005 |

(Continued)

OTHER PUBLICATIONS

Acculeaf Brochure, www.direxgroup.com, version 804AS, Mar. 8, 2009, 6 pages.
(Continued)

*Primary Examiner* — Thomas R Artman
(74) *Attorney, Agent, or Firm* — Pillsbury Winthrop Shaw Pittman LLP

(57) ABSTRACT

A system including a diagnostic-quality CT scanner for imaging a patient, the diagnostic-quality CT scanner having an imaging isocenter and a radiation therapy device positioned adjacent the diagnostic-quality CT scanner, the radiation therapy device including a gantry carrying a radiation therapy beam source and having a radiation therapy isocenter separate from the imaging isocenter of the diagnostic-quality CT scanner. The system including a couch configured to position the patient for imaging and for radiation therapy by translating the patient between the diagnostic quality CT scanner and the radiation therapy device.

8 Claims, 15 Drawing Sheets

Related U.S. Application Data

(60) Provisional application No. 62/433,745, filed on Dec. 13, 2016.

(51) Int. Cl.
  *G21K 1/04* (2006.01)
  *A61B 6/06* (2006.01)

(52) U.S. Cl.
  CPC ......... *A61N 5/1037* (2013.01); *A61N 5/1045* (2013.01); *A61N 5/1049* (2013.01); *A61N 5/1069* (2013.01); *G21K 1/046* (2013.01); *A61B 6/06* (2013.01); *A61N 5/1039* (2013.01); *A61N 5/1043* (2013.01); *A61N 2005/1052* (2013.01); *A61N 2005/1061* (2013.01); *A61N 2005/1063* (2013.01); *A61N 5/1065* (2013.01); *A61N 2005/1094* (2013.01)

(56) References Cited

U.S. PATENT DOCUMENTS

| | | | |
|---|---|---|---|
| 4,233,662 A | 11/1980 | Lemay | |
| 4,463,266 A | 7/1984 | Brahme | |
| 4,481,657 A | 11/1984 | Larsson | |
| 4,589,126 A | 5/1986 | Augustsson | |
| 4,672,212 A | 6/1987 | Brahme | |
| 4,694,837 A | 9/1987 | Blakeley | |
| 4,771,785 A | 9/1988 | Duer | |
| 4,851,778 A | 7/1989 | Kaufman | |
| 4,987,309 A | 1/1991 | Klasen | |
| 5,027,818 A | 7/1991 | Bova | |
| 5,039,867 A | 8/1991 | Nishihara | |
| 5,094,837 A | 3/1992 | Bis | |
| 5,117,829 A | 6/1992 | Miller | |
| 5,166,531 A | 11/1992 | Huntzinger | |
| 5,216,255 A | 6/1993 | Weidlich | |
| 5,317,616 A | 5/1994 | Swerdloff | |
| 5,327,884 A | 7/1994 | Hardy | |
| 5,328,681 A | 7/1994 | Kito | |
| 5,332,908 A | 7/1994 | Weidlich | |
| 5,351,280 A | 9/1994 | Swerdloff | |
| 5,365,927 A | 11/1994 | Roemer | |
| 5,373,844 A | 12/1994 | Smith | |
| 5,377,678 A | 1/1995 | Dumoulin | |
| 5,378,989 A | 1/1995 | Barber | |
| 5,391,139 A | 2/1995 | Edmundson | |
| 5,412,823 A | 5/1995 | Sitta | |
| 5,442,675 A | 8/1995 | Swerdloff | |
| 5,443,068 A | 8/1995 | Cline | |
| 5,458,125 A | 10/1995 | Schweikard | |
| 5,511,549 A | 4/1996 | Legg | |
| 5,513,238 A | 4/1996 | Leber | |
| 5,537,452 A | 7/1996 | Shepherd | |
| 5,538,494 A | 7/1996 | Matsuda | |
| 5,547,454 A | 8/1996 | Horn | |
| 5,555,283 A | 9/1996 | Shiu | |
| 5,591,983 A | 1/1997 | Yao | |
| 5,596,619 A | 1/1997 | Carol | |
| 5,602,892 A | 2/1997 | Llacer | |
| 5,602,982 A | 2/1997 | Llacer | |
| 5,647,361 A | 7/1997 | Damadian | |
| 5,659,281 A | 8/1997 | Pissanetzky | |
| 5,722,411 A | 3/1998 | Suzuki | |
| 5,724,400 A | 3/1998 | Swerdloff | |
| 5,734,384 A | 3/1998 | Yanof | |
| 5,740,225 A | 4/1998 | Nabatame | |
| 5,748,700 A | 5/1998 | Shepherd | |
| 5,751,781 A | 5/1998 | Brown | |
| 5,757,881 A | 5/1998 | Hughes | |
| 5,790,996 A | 8/1998 | Narfstrom | |
| 5,802,136 A | 9/1998 | Carol | |
| 5,815,547 A | 9/1998 | Shepherd | |
| 5,851,182 A | 12/1998 | Sahadevan | |
| 5,889,834 A | 3/1999 | Vilsmeier | |
| 5,894,503 A | 4/1999 | Shepherd | |
| 5,993,373 A | 11/1999 | Nonaka | |
| 6,005,916 A | 12/1999 | Johnson | |
| 6,038,283 A | 3/2000 | Carol | |
| 6,052,430 A | 4/2000 | Siochi | |
| 6,052,436 A | 4/2000 | Huttner | |
| 6,083,167 A * | 7/2000 | Fox | G16H 20/40 600/439 |
| 6,094,760 A | 8/2000 | Nonaka | |
| 6,104,779 A | 8/2000 | Shepherd | |
| 6,112,112 A | 8/2000 | Gilhuijs | |
| 6,125,335 A | 9/2000 | Simon | |
| 6,144,875 A | 11/2000 | Schweikard | |
| 6,175,761 B1 | 1/2001 | Frandsen | |
| 6,198,957 B1 | 3/2001 | Green | |
| 6,207,952 B1 | 3/2001 | Kan | |
| 6,223,067 B1 | 4/2001 | Vilsmeier | |
| 6,240,162 B1 | 5/2001 | Hernandez-Guerra | |
| 6,260,005 B1 | 7/2001 | Yang | |
| 6,273,858 B1 * | 8/2001 | Fox | A61B 8/4245 600/467 |
| 6,278,891 B1 | 8/2001 | Reiderman | |
| 6,314,159 B1 | 11/2001 | Siochi | |
| 6,330,300 B1 | 12/2001 | Siochi | |
| 6,349,129 B1 | 2/2002 | Siochi | |
| 6,366,798 B2 | 4/2002 | Green | |
| 6,373,250 B1 | 4/2002 | Tsoref | |
| 6,381,486 B1 | 4/2002 | Mistretta | |
| 6,385,286 B1 | 5/2002 | Fitchard | |
| 6,385,477 B1 | 5/2002 | Werner | |
| 6,393,096 B1 | 5/2002 | Carol | |
| 6,405,072 B1 | 6/2002 | Cosman | |
| 6,411,675 B1 | 6/2002 | Llacer | |
| 6,414,487 B1 | 7/2002 | Anand | |
| 6,422,748 B1 | 7/2002 | Shepherd | |
| 6,424,856 B1 | 7/2002 | Vilsmeier | |
| 6,459,769 B1 | 10/2002 | Cosman | |
| 6,466,813 B1 | 10/2002 | Shukla | |
| 6,487,435 B2 | 11/2002 | Mistretta | |
| 6,504,899 B2 | 1/2003 | Pugachev | |
| 6,512,813 B1 | 1/2003 | Krispel | |
| 6,512,942 B1 | 1/2003 | Burdette | |
| 6,516,046 B1 | 2/2003 | Frohlich | |
| 6,526,123 B2 | 2/2003 | Ein-Gal | |
| 6,527,443 B1 | 3/2003 | Vilsmeier | |
| 6,542,767 B1 | 4/2003 | Mcnichols | |
| 6,546,073 B1 | 4/2003 | Lee | |
| 6,560,311 B1 | 5/2003 | Shepard | |
| 6,564,084 B2 | 5/2003 | Allred | |
| 6,570,475 B1 | 5/2003 | Lvovsky | |
| 6,584,174 B2 | 6/2003 | Schubert | |
| 6,594,516 B1 | 7/2003 | Steckner | |
| 6,600,810 B1 | 7/2003 | Hughes | |
| 6,609,022 B2 | 8/2003 | Vilsmeier | |
| 6,611,700 B1 | 8/2003 | Vilsmeier | |
| 6,618,467 B1 | 9/2003 | Ruchala | |
| 6,636,645 B1 | 10/2003 | Yu | |
| 6,657,391 B2 | 12/2003 | Ding | |
| 6,661,870 B2 | 12/2003 | Kapatoes | |
| 6,708,054 B2 | 3/2004 | Shukla | |
| 6,719,683 B2 | 4/2004 | Frohlich | |
| 6,724,922 B1 | 4/2004 | Vilsmeier | |
| 6,728,336 B2 | 4/2004 | Bortfeld | |
| 6,731,970 B2 | 5/2004 | Schlossbauer | |
| 6,735,277 B2 | 5/2004 | Mcnutt | |
| 6,757,355 B1 | 6/2004 | Siochi | |
| 6,772,002 B2 | 8/2004 | Schmidt | |
| 6,778,850 B1 | 8/2004 | Adler | |
| 6,792,074 B2 | 9/2004 | Erbel | |
| 6,849,129 B2 | 2/2005 | Bilz et al. | |
| 6,853,704 B2 | 2/2005 | Collins | |
| 6,859,660 B2 | 2/2005 | Vilsmeier | |
| 6,862,469 B2 | 3/2005 | Bucholz | |
| 6,865,253 B2 | 3/2005 | Blumhofer | |
| 6,865,411 B2 | 3/2005 | Erbel | |
| 6,879,714 B2 | 4/2005 | Hutter | |
| 6,885,886 B2 | 4/2005 | Bauch | |
| 6,891,375 B2 | 5/2005 | Goto | |
| 6,891,924 B1 | 5/2005 | Yoda | |
| 6,898,456 B2 | 5/2005 | Erbel | |

(56) References Cited

U.S. PATENT DOCUMENTS

| | | |
|---|---|---|
| 6,915,005 B1 | 7/2005 | Ruchala |
| 6,937,696 B1 | 8/2005 | Mostafavi |
| 6,947,582 B1 | 9/2005 | Vilsmeier |
| 6,965,847 B2 | 11/2005 | Wessol |
| 6,980,679 B2 | 12/2005 | Jeung |
| 6,999,555 B2 | 2/2006 | Morf |
| 7,012,385 B1 | 3/2006 | Kulish |
| 7,046,762 B2 | 5/2006 | Lee |
| 7,046,765 B2 | 5/2006 | Wong |
| 7,046,831 B2 | 5/2006 | Ruchala |
| 7,050,845 B2 | 5/2006 | Vilsmeier |
| 7,092,573 B2 | 8/2006 | Luo |
| 7,095,823 B2 | 8/2006 | Topolnjak |
| 7,096,055 B1 | 8/2006 | Schweikard |
| 7,123,758 B2 | 10/2006 | Jeung |
| 7,130,372 B2 | 10/2006 | Kusch |
| 7,154,991 B2 | 12/2006 | Earnst |
| 7,162,005 B2 | 1/2007 | Bjorkholm |
| 7,166,852 B2 | 1/2007 | Saracen |
| 7,167,542 B2 | 1/2007 | Juschka |
| 7,171,257 B2 | 1/2007 | Thomson |
| 7,180,366 B2 | 2/2007 | Roos |
| 7,191,100 B2 | 3/2007 | Mostafavi |
| 7,202,663 B2 | 4/2007 | Huang |
| 7,204,640 B2 | 4/2007 | Fu |
| 7,221,733 B1 | 5/2007 | Takai |
| 7,227,925 B1 | 6/2007 | Mansfield |
| 7,230,429 B1 | 6/2007 | Huang |
| 7,231,075 B2 | 6/2007 | Raghavan |
| 7,231,076 B2 | 6/2007 | Fu |
| 7,260,426 B2 | 8/2007 | Schweikard |
| 7,265,545 B2 | 9/2007 | Krueger |
| 7,266,175 B1 | 9/2007 | Romesberg |
| 7,266,176 B2 | 9/2007 | Allison |
| 7,289,599 B2 | 10/2007 | Seppi |
| 7,298,819 B2 | 11/2007 | Dooley |
| 7,302,038 B2 | 11/2007 | Mackie |
| 7,315,636 B2 | 1/2008 | Kuduvalli |
| 7,317,782 B2 | 1/2008 | Bjorkholm |
| 7,318,805 B2 | 1/2008 | Schweikard |
| 7,324,626 B2 | 1/2008 | Vilsmeier |
| 7,327,865 B2 | 2/2008 | Fu |
| 7,366,278 B2 | 4/2008 | Fu |
| 7,386,099 B1 | 6/2008 | Kasper |
| 7,394,081 B2 | 7/2008 | Okazaki |
| 7,403,638 B2 | 7/2008 | Jeung |
| 7,412,029 B2 | 8/2008 | Myles |
| 7,415,095 B2 | 8/2008 | Wofford |
| 7,423,273 B2 | 9/2008 | Clayton |
| 7,426,318 B2 | 9/2008 | Fu |
| 7,444,178 B2 | 10/2008 | Goldbach |
| 7,450,687 B2 * | 11/2008 | Yeo .............. A61N 5/1031 378/65 |
| 7,463,823 B2 | 12/2008 | Birkenbach |
| 7,471,813 B2 | 12/2008 | Ulmer |
| 7,477,776 B2 | 1/2009 | Lachner |
| 7,480,399 B2 | 1/2009 | Fu |
| 7,505,037 B2 | 3/2009 | Wang |
| 7,505,617 B2 | 3/2009 | Fu |
| 7,522,779 B2 | 4/2009 | Fu |
| 7,532,705 B2 | 5/2009 | Yin |
| 7,542,622 B1 | 6/2009 | Angelini |
| 7,558,617 B2 | 7/2009 | Vilsmeier |
| 7,570,987 B2 | 8/2009 | Raabe |
| 7,577,474 B2 | 8/2009 | Vilsmeier |
| 7,589,326 B2 | 9/2009 | Mollov |
| 7,596,209 B2 | 9/2009 | Perkins |
| 7,634,122 B2 | 12/2009 | Bertram |
| 7,636,417 B2 | 12/2009 | Bjorkholm |
| 7,638,752 B2 | 12/2009 | Partain |
| 7,640,607 B2 | 1/2010 | Guertin |
| 7,657,304 B2 | 2/2010 | Mansfield |
| 7,659,718 B1 | 2/2010 | Lustig |
| 7,688,998 B2 | 3/2010 | Tuma |
| 7,728,311 B2 | 6/2010 | Gall |
| 7,741,624 B1 | 6/2010 | Sahadevan |
| 7,785,358 B2 | 8/2010 | Lach |
| 7,791,338 B2 | 9/2010 | Kim |
| 7,840,045 B2 | 11/2010 | Guo |
| 7,901,357 B2 | 3/2011 | Boctor |
| 7,902,530 B1 | 3/2011 | Sahadevan |
| 7,907,987 B2 | 3/2011 | Dempsey |
| 7,916,840 B2 | 3/2011 | Noguchi |
| 7,957,507 B2 | 6/2011 | Cadman |
| 7,983,380 B2 | 7/2011 | Guertin |
| 8,139,714 B1 | 3/2012 | Sahadevan |
| 8,155,417 B2 | 4/2012 | Piron |
| 8,173,983 B1 | 5/2012 | Sahadevan |
| 8,190,233 B2 | 5/2012 | Dempsey |
| 8,214,010 B2 | 7/2012 | Courtney |
| 8,306,185 B2 * | 11/2012 | Bal ................ G16H 20/40 378/65 |
| 8,310,233 B2 | 11/2012 | Trzasko |
| 8,331,531 B2 | 12/2012 | Fahrig |
| 8,406,844 B2 | 3/2013 | Ruchala |
| 8,460,195 B2 | 6/2013 | Courtney |
| 8,536,547 B2 | 9/2013 | Maurer, Jr. |
| 8,637,841 B2 | 1/2014 | Prince |
| 8,803,524 B2 | 8/2014 | Dempsey |
| 8,812,077 B2 | 8/2014 | Dempsey |
| 8,836,332 B2 | 9/2014 | Shvartsman |
| 8,983,573 B2 | 3/2015 | Carlone |
| 8,989,845 B2 | 3/2015 | Brinks |
| 9,082,520 B2 | 7/2015 | Prince |
| 9,114,253 B2 | 8/2015 | Dempsey |
| 9,211,423 B2 | 12/2015 | Gross |
| 9,289,626 B2 | 3/2016 | Kawrakow |
| 9,324,468 B2 | 4/2016 | Mansfield |
| 9,421,398 B2 | 8/2016 | Shvartsman |
| 9,423,477 B2 | 8/2016 | Dempsey |
| 9,446,263 B2 | 9/2016 | Dempsey |
| 9,472,000 B2 | 10/2016 | Dempsey |
| 9,526,918 B2 | 12/2016 | Kruip |
| 9,687,200 B2 | 6/2017 | Maurer, Jr. |
| 9,966,160 B2 | 5/2018 | Kawrykow |
| 10,124,190 B2 | 11/2018 | Ojha |
| 10,463,882 B2 | 11/2019 | Liu |
| 10,478,138 B2 | 11/2019 | Tian |
| 10,737,122 B2 | 8/2020 | Weidlich |
| 11,000,706 B2 * | 5/2021 | Kawrykow .......... A61N 5/1031 |
| 2001/0043669 A1 | 11/2001 | Ein-Gal |
| 2001/0049475 A1 | 12/2001 | Bucholz |
| 2002/0046010 A1 | 4/2002 | Wessol |
| 2002/0091315 A1 | 7/2002 | Spetz |
| 2002/0131556 A1 | 9/2002 | Steinberg |
| 2002/0150207 A1 | 10/2002 | Kapatoes |
| 2002/0151786 A1 | 10/2002 | Shukla |
| 2002/0193685 A1 | 12/2002 | Mate |
| 2003/0011451 A1 | 1/2003 | Katznelson |
| 2003/0057947 A1 | 3/2003 | Ni |
| 2003/0068097 A1 | 4/2003 | Wilson |
| 2003/0083901 A1 | 5/2003 | Bosch |
| 2003/0086526 A1 | 5/2003 | Clark |
| 2003/0112922 A1 | 6/2003 | Burdette |
| 2003/0155530 A1 | 8/2003 | Adnani |
| 2003/0181804 A1 | 9/2003 | Gagnon |
| 2003/0219098 A1 | 11/2003 | Mcnutt |
| 2004/0030240 A1 | 2/2004 | Kimura |
| 2004/0054248 A1 | 3/2004 | Kimchy |
| 2004/0106869 A1 | 6/2004 | Tepper |
| 2004/0184578 A1 | 9/2004 | Nakano |
| 2004/0254448 A1 | 12/2004 | Amies |
| 2004/0254773 A1 | 12/2004 | Zhang |
| 2005/0020917 A1 | 1/2005 | Scherch |
| 2005/0053267 A1 | 3/2005 | Mostafavi |
| 2005/0054916 A1 | 3/2005 | Mostafavi |
| 2005/0065431 A1 | 3/2005 | Reiderman |
| 2005/0143965 A1 | 6/2005 | Failla |
| 2005/0197564 A1 | 9/2005 | Dempsey |
| 2005/0201516 A1 * | 9/2005 | Ruchala ................ A61N 5/103 378/65 |
| 2005/0207531 A1 | 9/2005 | Dempsey |
| 2005/0254623 A1 | 11/2005 | Kamath |
| 2006/0058636 A1 | 3/2006 | Wemple |

(56) References Cited

U.S. PATENT DOCUMENTS

| | | |
|---|---|---|
| 2006/0074292 A1 | 4/2006 | Thomson |
| 2006/0120583 A1 | 6/2006 | Dewaele |
| 2006/0170679 A1 | 8/2006 | Wang |
| 2006/0193441 A1 | 8/2006 | Cadman |
| 2006/0280287 A1 | 12/2006 | Esham |
| 2006/0291621 A1 | 12/2006 | Yan |
| 2007/0003010 A1 | 1/2007 | Guertin |
| 2007/0003021 A1 | 1/2007 | Guertin |
| 2007/0014391 A1 | 1/2007 | Mostafavi |
| 2007/0016014 A1 | 1/2007 | Hara |
| 2007/0038058 A1 | 2/2007 | West |
| 2007/0043286 A1 | 2/2007 | Lu |
| 2007/0071169 A1* | 3/2007 | Yeo ............... A61N 5/1031 378/65 |
| 2007/0083114 A1 | 4/2007 | Yang |
| 2007/0086569 A1 | 4/2007 | Johnsen |
| 2007/0176126 A1 | 8/2007 | Hashimoto |
| 2007/0197908 A1 | 8/2007 | Ruchala |
| 2007/0230770 A1 | 10/2007 | Kulkarni |
| 2007/0244386 A1 | 10/2007 | Steckner |
| 2008/0033287 A1 | 2/2008 | Schwarze |
| 2008/0049897 A1 | 2/2008 | Molloy |
| 2008/0093567 A1 | 4/2008 | Gall |
| 2008/0108894 A1 | 5/2008 | Elgavish |
| 2008/0123927 A1 | 5/2008 | Miga |
| 2008/0177138 A1 | 7/2008 | Courtney |
| 2008/0197842 A1 | 8/2008 | Lustig |
| 2008/0205597 A1 | 8/2008 | Ono |
| 2008/0208036 A1 | 8/2008 | Amies |
| 2008/0235052 A1 | 9/2008 | Node-Langlois |
| 2008/0303457 A1 | 12/2008 | Maltz |
| 2008/0312526 A1 | 12/2008 | Gagnon |
| 2009/0039886 A1 | 2/2009 | White |
| 2009/0060130 A1 | 3/2009 | Wilkens |
| 2009/0129545 A1 | 5/2009 | Adler |
| 2009/0129659 A1 | 5/2009 | Deutschmann |
| 2009/0149735 A1 | 6/2009 | Fallone |
| 2009/0161826 A1 | 6/2009 | Gertner |
| 2009/0171184 A1 | 7/2009 | Jenkins |
| 2009/0175418 A1 | 7/2009 | Sakurai |
| 2009/0209844 A1 | 8/2009 | Gagnon |
| 2009/0264768 A1 | 10/2009 | Courtney |
| 2010/0033186 A1 | 2/2010 | Overweg |
| 2010/0040197 A1 | 2/2010 | Maniawski |
| 2010/0056900 A1 | 3/2010 | Whitcomb |
| 2010/0113911 A1 | 5/2010 | Dempsey |
| 2010/0119032 A1 | 5/2010 | Yan |
| 2010/0189220 A1 | 7/2010 | Flynn |
| 2010/0239066 A1 | 9/2010 | Fahrig |
| 2010/0312095 A1 | 12/2010 | Jenkins |
| 2010/0312100 A1 | 12/2010 | Zarkh |
| 2010/0322497 A1 | 12/2010 | Dempsey |
| 2011/0012593 A1 | 1/2011 | Shvartsman |
| 2011/0051893 A1 | 3/2011 | Mcnutt |
| 2011/0103551 A1* | 5/2011 | Bal ............... A61N 5/103 378/65 |
| 2011/0118588 A1 | 5/2011 | Komblau |
| 2011/0121832 A1 | 5/2011 | Shvartsman |
| 2011/0142887 A1 | 6/2011 | Har-Noy |
| 2011/0150180 A1 | 6/2011 | Balakin |
| 2011/0218420 A1 | 9/2011 | Carlone |
| 2011/0237859 A1 | 9/2011 | Kuhn |
| 2011/0241684 A1 | 10/2011 | Dempsey |
| 2011/0284757 A1 | 11/2011 | Butuceanu |
| 2011/0288407 A1 | 11/2011 | Brinks |
| 2011/0301449 A1 | 12/2011 | Maurer, Jr. |
| 2011/0313231 A1 | 12/2011 | Guertin |
| 2012/0022363 A1 | 1/2012 | Dempsey |
| 2012/0043482 A1 | 2/2012 | Prince |
| 2012/0070056 A1 | 3/2012 | Krueger |
| 2012/0150017 A1 | 6/2012 | Yamaya |
| 2012/0157402 A1 | 6/2012 | Cao |
| 2012/0165652 A1 | 6/2012 | Dempsey |
| 2012/0189102 A1 | 7/2012 | Maurer, Jr. |
| 2012/0245453 A1 | 9/2012 | Tryggestad |
| 2012/0253172 A1 | 10/2012 | Loeffler |
| 2013/0066135 A1 | 3/2013 | Rosa |
| 2013/0086163 A1 | 4/2013 | Neff |
| 2013/0090549 A1 | 4/2013 | Meltsner |
| 2013/0147476 A1 | 6/2013 | Shvartsman |
| 2013/0158382 A1 | 6/2013 | Chao |
| 2013/0245425 A1 | 9/2013 | Dempsey |
| 2013/0261429 A1 | 10/2013 | Lee |
| 2013/0267830 A1 | 10/2013 | Ojha |
| 2013/0296687 A1 | 11/2013 | Dempsey |
| 2013/0345545 A1 | 12/2013 | Gross |
| 2013/0345556 A1 | 12/2013 | Courtney |
| 2014/0003023 A1 | 1/2014 | Weibler |
| 2014/0084926 A1 | 3/2014 | Amthor |
| 2014/0112453 A1 | 4/2014 | Prince |
| 2014/0121495 A1 | 5/2014 | Dempsey |
| 2014/0135615 A1 | 5/2014 | Krulp |
| 2014/0263990 A1 | 9/2014 | Kawrykow |
| 2014/0266206 A1 | 9/2014 | Dempsey |
| 2014/0266208 A1 | 9/2014 | Dempsey |
| 2014/0275963 A1 | 9/2014 | Shvartsman |
| 2014/0330108 A1 | 11/2014 | Dempsey |
| 2014/0336442 A1 | 11/2014 | Keppel |
| 2014/0347053 A1 | 11/2014 | Dempsey |
| 2015/0065860 A1 | 3/2015 | Shvartsman |
| 2015/0077118 A1 | 3/2015 | Shvartsman |
| 2015/0095044 A1 | 4/2015 | Hartman |
| 2015/0154756 A1 | 6/2015 | Gerganov |
| 2015/0165233 A1 | 6/2015 | Dempsey |
| 2015/0185300 A1 | 7/2015 | Shvartsman |
| 2015/0273239 A1 | 10/2015 | Hsu |
| 2016/0146911 A1 | 5/2016 | Chmielewski |
| 2016/0158382 A1 | 6/2016 | Leonidov |
| 2016/0184609 A1 | 6/2016 | Dempsey |
| 2016/0232690 A1 | 8/2016 | Ahmad |
| 2016/0287904 A1 | 10/2016 | Liu |
| 2016/0303401 A1 | 10/2016 | Mostafavi |
| 2016/0334479 A1 | 11/2016 | Poole |
| 2016/0356869 A1 | 12/2016 | Dempsey |
| 2017/0001039 A1 | 1/2017 | Dempsey |
| 2017/0014644 A1 | 1/2017 | Shvartsman |
| 2017/0021198 A1 | 1/2017 | Kawrykow |
| 2017/0148536 A1 | 5/2017 | Kawrykow |
| 2017/0203126 A1 | 7/2017 | Dempsey |
| 2017/0231583 A1 | 8/2017 | Goteti Venkata |
| 2017/0252577 A1 | 9/2017 | Dempsey |
| 2017/0273643 A1 | 9/2017 | Maurer, Jr. |
| 2017/0371001 A1 | 12/2017 | Dempsey |
| 2018/0021595 A1 | 1/2018 | Kesti-Helia |
| 2018/0078785 A1 | 3/2018 | Ollila |
| 2018/0078792 A1 | 3/2018 | Ollila |
| 2018/0133511 A1 | 5/2018 | Dempsey |
| 2018/0161602 A1 | 6/2018 | Kawrykow |
| 2018/0185669 A1 | 7/2018 | Kuusela |
| 2018/0243584 A1 | 8/2018 | Nord |
| 2018/0261351 A1 | 9/2018 | Kawrykow |
| 2018/0280733 A1 | 10/2018 | Weidlich |
| 2019/0083814 A1 | 3/2019 | Tallinen |
| 2019/0159845 A1 | 5/2019 | Dempsey |
| 2021/0220676 A1* | 7/2021 | Kawrykow ......... A61N 5/1045 |

FOREIGN PATENT DOCUMENTS

| | | |
|---|---|---|
| CN | 1946339 A | 4/2007 |
| CN | 101000689 A | 7/2007 |
| CN | 101267858 A | 9/2008 |
| CN | 101268474 A | 9/2008 |
| CN | 101278361 A | 10/2008 |
| CN | 101443819 A | 5/2009 |
| CN | 102369529 A | 3/2012 |
| CN | 102472830 A | 5/2012 |
| CN | 102641561 A | 8/2012 |
| CN | 104161532 | 11/2014 |
| DE | 3828639 A1 | 3/1989 |
| EP | 0562644 | 9/1993 |
| EP | 2359905 A1 | 8/2011 |
| EP | 2424430 B1 | 1/2013 |
| FR | 2839894 A1 | 11/2003 |
| GB | 2393373 A | 3/2004 |

(56) References Cited

FOREIGN PATENT DOCUMENTS

| | | |
|---|---|---|
| JP | 63294839 | 12/1988 |
| JP | H1206300 A | 8/1989 |
| JP | 03009767 | 1/1991 |
| JP | 06054916 | 1/1994 |
| JP | H11216197 | 8/1999 |
| JP | 2001517132 A | 10/2001 |
| JP | 2002186676 A | 7/2002 |
| JP | 2002210026 | 7/2002 |
| JP | 2002210026 A | 7/2002 |
| JP | 2002522129 A | 7/2002 |
| JP | 2003210595 A | 7/2003 |
| JP | 2005103295 A | 4/2005 |
| JP | 2006000220 | 1/2006 |
| JP | 2006149560 A | 6/2006 |
| JP | 2007526036 A | 9/2007 |
| JP | 2009501043 A | 1/2009 |
| JP | 2009511222 A | 3/2009 |
| JP | 2009160300 A | 7/2009 |
| JP | 2009538195 A | 11/2009 |
| JP | 2010269067 A | 12/2010 |
| JP | 2015520631 | 7/2015 |
| WO | 1994028974 | 12/1994 |
| WO | 1999032189 | 7/1999 |
| WO | 2000025864 | 5/2000 |
| WO | 2001027939 | 4/2001 |
| WO | 2002072190 A2 | 9/2002 |
| WO | 20030008986 | 1/2003 |
| WO | 2004024235 A1 | 3/2004 |
| WO | 2005081842 A2 | 9/2005 |
| WO | 2006007277 A2 | 1/2006 |
| WO | 2006097274 A1 | 9/2006 |
| WO | 2007007276 A2 | 1/2007 |
| WO | 2007014105 A2 | 2/2007 |
| WO | 2007045076 A1 | 4/2007 |
| WO | 2007126842 A2 | 11/2007 |
| WO | 2008013598 A2 | 1/2008 |
| WO | 2009155700 A1 | 12/2009 |
| WO | 2010103644 A1 | 9/2010 |
| WO | 2010113050 A2 | 10/2010 |
| WO | 2011008969 A1 | 1/2011 |
| WO | 2012045153 | 4/2012 |
| WO | 2012069965 | 5/2012 |
| WO | 2012164527 A1 | 12/2012 |
| WO | 20150138945 | 9/2015 |

OTHER PUBLICATIONS

B W Raaymakers et al.; "Integrating a 1.5 T MRI Scanner with a 6 MV Accelerator: Proof of Concepts," Physics in Medicine and Biology. vol. 54, No. 12, May 19, 2009, pp. N229-N237, XP055395399, Bristol GB ISSN: 0031-9155. 9 pages.
Balter, James M., et al. 'Accuracy of a Wireless Localization System for Radiotherapy' Int. J. Radiation Oncology Biol. Phys., vol. 61, No. 3. pp. 933-937, Nov. 1, 2004, Elsevier Inc., USA.
Baro, J et al. 'Penelope: an algorithm for Monte Carlo simulation of the penetration and energy loss of electrons and positrons in matter' Nuclear Instruments and Methods in Physics Research B 100 (1995) 31-46, received Sep. 30, 1994, Elsevier Science B.V.
Barth, et al. "Simultaneous Multislice (SMS) Imaging Techniques." Magnetic Resonance in Medicine; vol. 75; pp. 63-81; 2016.
Bayouth, "Siemens Multileaf Collimator Characterization and Quality Assurance Approaches for Intensity-Modulation Readiotherapy," Int. J. Radiation Oncology Biol. Phys., vol. 71, No. 1, Supplement, pp. S93-S97, 2008.
Bemier, Jacques et al. 'Radiation oncology: a century of achievements' Nature Reviews-Cancer, vol. 4, Sep. 2004. pp. 737-747.
Bilgin, A. et al. 'Randomly Perturbed Radial Trajectories for Compressed Sensing MRI.' Proceedings of International Society for Magnetic Resonance in Medicine 16 (2008):p. 3152.
Blaimer, et al. 'Smash, Sense, Pills, Grappa, How to Choose the Optimal Method'. Top Magan Reson Imaging, vol. 15, No. 4, Aug. 2004, pp. 223-236.
Boyer, et al., "Basic Applications of Multileaf Collimators," AAPM Report No. 72, Jul. 2001, 62 pages.
Buchanan, Roger 'Cobalt on the way out' British Medical Journal, vol. 292, Feb. 1, 1986. p. 290.
Candes, et al. 'Robust Uncertainty Principles: Exact Signal Reconstruction from Highly Incomplete Frequency Information.' IEEE Transactions on Information Theory, vol. 52, No. 2, Feb. 2006, pp. 489-509.
Candes, et al. 'Sparsity and Incoherence in Compressive Sampling'. Electrical and Computer Engineering, Georgia Tech, Atlanta, GA, 90332. Nov. 2006, pp. 1-20.
Chng, N. et al. 'Development of inverse planning and limited angle CT reconstruction for cobalt-60 tomotherapy' Proceedings of 51st Annual Meeting of Canadian Organization of Medical Physicists and the Canadian College of Physicists in Medicine, 2005, McMaster University, Hamilton Ontario. Medical Physics, 2005, p. 2426. (4 pages).
CIPRA 'L1-magic' from SIAM News, vol. 39, No. 9, Nov. 2006. (3 pages).
Cosgrove, et al., "Commissioning of a micro multi-leaf collimator and planning system for stereotactic radio surgery," Radiotherapy and Oncology 50 (1999) 325-336.
Crop, et al., "Monte Carlo modeling of the ModuLeaf miniature MLC for small field dosimetry and quality assurance of the clinical treatment planning system," Phys. Med. Biol. 52 (2007) 3275-3290.
Cui, et al., "Optimizing leaf widths for a multileaf collimator," Phys. Med. Biol. 54 (2009) 3051-3062, Apr. 2009 paper.
Cui, et al., "The configuratin designs for multileaf collimeters," Depart. of Radiation Oncology, Cancer Hospital (Institute), Chinese Academy of Medical Science, Beijing 100021, China, Medical Equipment, vol. 22, No. 2, Sep. 19, 2008, 21 pages.
Dai, et al., "A finger leaf design for dual layer MLCs," O. Dössel and W.C. Schlegel (Eds.): WC 2009, IFMBE Proceedings 25/1, pp. 696-699, 2009.
De Poorter J. et al. 'Noninvasive MRI Thermometry with the Proton Resonance Frequencey (PRF) Method: In Vivo Results in Human Muscle,' Magnetic Resonance in Medicine, Academic Press, Duluth, vol. 33, No. 1, Jan. 1995 pp. 74-81 XP000482971.
Donoho, David L., 'Compressed Sensing'. Department of Statistics, Stanford University. Sep. 14, 2004. (34 pages).
EP App. No. 10195476.6; Extended EP Search Report dated Jul. 4, 2011; 11 pages.
EP App. No. 10800553.9; Extended EP Search Report dated Oct. 17, 2013; 10 pages.
EP App. No. 17000760.3; Extended EP Search Report dated Nov. 9, 2017; 7 pages.
Excerpt from "Topics on Biomedical Physics" from www.worldscientific.com: Williams, "Commissioning and Clinical Application of the Phillips Multileaf Collimator," North Western Medical Physics Department, the Christie Hospital, Manchester, UK, Jun. 24, 1991, pp. 148-154.
Extended European Search Report in European Patent Application No. EP11850577, dated Jul. 9, 2014. 8 pages.
Fischer, et al., "Commissioning of a double-focused micro multileaf collimator (pMLC)," Journal of Applied Clinical Medical Physics, vol. 11, No. 2, Spring 2010, pp. 81-91.
Foroosh, Hassan, et.al. 'Extension of Phase Correlation to Subpixel Registration.' IEEE Transactions on Image Processing, vol. 11, No. 3, 2002, pp. 188-200.
Garcia-Garduno, et. al., "Radiation transmission, leakage and beam penumbra measurements of a micro-multileaf collimator using GafChromic EBT film," Journal of Applied Clinical Medical Physics, vol. 9, No. 3, Summer 2008, pp. 90-98.
Gerganov G et al, 'Portal image registration using the phase correlation method', 2013 IEEE Nuclear Science Symposium and Medical Imaging Conference (2013 NSS/MIC), IEEE, (Oct. 27, 2013), doi:10.1109/NSSMIC.2013.6829306, pp. 1-3, XP032601397.
Giantsoudi, et al., "Monte Carlo Modeling and Commissioning of a Dual-layer Micro Multileaf Collimator," Technology in Cancer Research & Treatment, vol. 8, No. 2, Apr. 2009, pp. 105-114.
Goitein, Michael. 'Organ and Tumor Motion: an Overview.' Seminars in Radiation Oncology. vol. 14, No. 1 (Jan. 2004: pp. 2-9.

(56) References Cited

OTHER PUBLICATIONS

Goldberg, S. Nahum; G. Scott Gazelle, and Peter R. Mueller. 'Thermal Ablation Therapy for Focal Malignancy: a Unified Approach to Underlying Principles, Techniques, and Diagnostic Imaging Guidance.' Amer. J. of Roentgenology, vol. 174, Feb. 2000 pp. 323-331 XP002431995.

Golen et al., "A comparison of two scoring systems for late radiation toxicity in patients after radiotherapy for head and neck cancer," Rep Pract Oncol Radiother, 2005; 10(4): 179-192.

Greer, et al., "A design for a dual assembly multileaf collimator," Medical Physics, vol. 27, No. 10, Oct. 2000, pp. 2242-2255.

Haacke, Mark E. et al. 'Constrained reconstruction: a superresolution, optimal signal-to-noise alternative to the Fourier transform in magnetic resonance imaging.' Medical Physics, AIP, Melville, NY, US, vol. 16, No. 3, May 1, 1989 (May 1, 1989), pp. 388-397, XP000034068, ISSN: 0094-2405, DDI: 10.1118/1.596427.

Hajdok, George. 'An Investigation of Megavoltage Computed Tomography Using a Radioactive Cobalt-60 Gamma Ray Source for Radiation Therapy Treatment Verification.' Thesis. May 2002. 150 pages.

Hartmann, et al., "Dosimetric characterization of a new miniature multileaf collimator," Phys. Med. Biol. 47 , 2002, pp. N171-N177.

Hernando, D. et al. 'Interventional MRI with sparse sampling: an application of compressed sensing.' Proceedings of International Society for Magnetic Resonance in Medicine. 16 (2008):p. 1482.

Hicks, et al., 'Early FDG-PET imaging after radical radiotherapy for non-small-cell lung cancer: Inflammatory changes in normal tissues correlate with tumor response and do not confound therapeutic response evaluation', International Journal of Radiation: Oncology Biology Physics; [Publication // Division of Scientific and Technical Information, International Atomic Energy Agency, ISSN 0074-1876 ; 1196], Pergamon Press, USA, (Oct. 1, 2004), vol. 60, No. 2, doi:10.1016/J.IJROBP.2004.03.036, ISSN 0360-3016, ISBN 978-92-0-107304-4, pp. 412-418, XP004582712.

Hong J et al, 'Interventional navigation for abdominal therapy based on simultaneous use of MRI and ultrasound', Medical and Biological Engineering and Computing, Springer, Heildelberg, DE, vol. 44, No. 12, doi:10.1007/S11517-006-0133-2, ISSN 0140-0118, (Nov. 11, 2006), pp. 1127-1134, (Nov. 11, 2006), XP001551805.

International Search Report and Written Opinion dated Apr. 13, 2012, for corresponding international application No. PCT/US2011/066605; 9 pages.

International Search Report of the International Searching Authority issued in International Application No. PCT/US2014/028792, dated Jul. 2, 2014. 3 pages.

Irarrazabal, Pablo, and Dwight G. Nishimura. 'Fast Three Dimensional Magnetic Resonance Imaging.' Magnetic Resonance in Medicine, vol. 33, No. 5, 1995, pp. 656-662.

Jaffray, David A., et al. 'Flat-Panel Cone Beam Computed Tomography for Image-Guided Radiation Therapy' Int. J. Radiation Oncology Biol. Phys., vol. 53, No. 5, pp. 1337-1349, Apr. 3, 2002, Elsevier Science Inc., USA.

Jan J. W. Lagendijk et al.; "MR Guidance in Radiotherapy", Physics in Medicine and Biology, Institute of Physics Publishing, Bristol GB, vol. 59, No. 21, Oct. 16, 2014, pp. R349-R369, XP020272054, ISSN: 0031-9155.

Jeraj, et al., "Multileaf collimator in radiotherapy," Radiol Oncol 2004; 38(3): 235-40.

Jursinic, Paul et al. 'Characteristics of secondary electrons produced by 6, 10 and 24 MV x-ray beams' Phys. Med. Biol. 41 (1996) 1499-1509, United Kingdom.

Khan, Faiz M., 'The Physics of Radiation Therapy (second edition)', Lippincott Williams & Wilkins. Chapter 13. 1985. pp. 323-332.

Lagendijk et al, 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061.

Lagendijk JJ W et al.: "MRI Guided Radiotherapy: a MRI based linear Accelerator", Radiotherapy and Oncology, vol. 56, No. 01, Sep. 21, 2000 (Sep. 21, 2000), pp. S60-S61.

Langen, K.M. et al. 'Organ Motion and its Management.' Int J. Radiation Oncology Biol. Phys., vol. 50, No. 1, pp. 265-278. 2001. Elsevier Science Inc., USA.

Law, C. , and Glover, G. 'Deconvolving Haemodynamic Response Function in fMRI under high noise by Compressive Sampling.' Proceedings of International Society for Magnetic Resonance in Medicine. 17 (2009):p. 1712. Stanford University, Stanford, CA, United States.

Li, Kang and Kanadae, Takeo. 'Nonnegative Mixed-Norm Preconditioning for Microscopy Image Segmentation.' Information Processing in Medical Imaging. Springer Berlin Heidelberg. vol. 5636. (2009):362-373.

Liang, J. and D. Yan. 'Reducing Uncertainties in Volumetric Image Based Deformable Organ Registration.' Medical Physics, vol. 30, No. 8, 2003, pp. 2116-2122.

Liu, et al., "Dosimetric characteristics of dual-layer multileaf collimation for small-field and intensity-modulated radiation therapy applications," Journal of Applied Clinical Medical Physics, vol. 9, No. 2, Spring 2008, pp. 15-29.

Lopez, Mike R. et al. 'Relativistic Magnetron Driven by a Microsecond E-Beam Accelerator with a Ceramic Insulator' IEEE Transactions on Plasma Science vol. 32, No. 3, Jun. 2004. pp. 1171-1180.

LoSasso, et al., "Physical and dosimetric aspects of a multileaf collimation system used in the dynamic mode for implementing intensity modulated radiotherapy," Med. Phys. 25 (10) Oct. 1998, pp. 1919-1927.

Lurie, D.J., PhD. 'Free radical imaging' The British Journal of Radiology. 74 (2001). pp. 782-784.

Lustig, et al. 'L1 SPIR-IT: Autocalibrating Parallel Imaging Compressed Sensing.' Electrical Engineering, Stanford University, Stanford, CA, United States. Radiology, Stanford University. Statistics, Stanford University (p. 334).

Lustig, M, et al. 'Faster Imaging with Randomly Perturbed, Undersampled Spirals and ILl_1 Reconstruction.' in: Proceedings of the 13th Annual Meeting of ISMRM, Miami Beach, 2005. (1 page).

Macura, Katarzyna J., MD, PhD. 'Advancements in Magnetic Resonance-Guided Robotic Interventions in the Prostate'. Top Magn Reson Imaging. vol. 19, No. 6. Dec. 2008. pp. 297-304.

Mah et al., "Measurement of intrafractional prostate motion using magnetic resonance imaging," Int. J. Radiation Oncology Boil. Phys. Vo.54, No. 2, pp. 568-575, 2002.

Mardirossian, et. al., "Commissioning of mini-multi-leaf-collimator (MMLC) for stereotactic radiosurgery and radiotherapy," Journal of X-Ray Science and Technology 11 (2003) 21-31.

May et al., Abnormal Signal Intensity in Skeletal Muscle at MR Imaging: Patterns, Pearls, and Pitfalls, RadioGraphics 2000; 20: S295-S315.

McMahon et al., "Muscle Edema", AJR:194, Apr. 2010, W284-W292.

Medtronic, Inc.. 'Image-Guided Surgery Overview'. 2010. 2 pages.

Meyer, et al. "Fast Spiral Coronary Artery Imaging", Magnetic Resonance in Medicine 28, pp. 202-213 (1992).

Millennium MLC Multileaf Collimator, Varian Medical Systems, Inc., www.varian.com, Copyright, 2001, pp. 1-10.

Mozer, Pierre C, MD, PhD. 'Robotic Image-Guided Needle Interventions of the Prostate'. Reviews in Urology. vol. 11, No. 1. 2009. pp. 7-15.

Muntener, Michael, MD et al. 'Transperineal Prostate Intervention: Robot for fully Automated MR Imaging-System Description and Proof of Principle in a Canine Model'. Radiology. vol. 247, No. 2. May 2008. pp. 543-549.

Muralidhar, et. al., "Measurement of back-scattered radiation from micro multileaf collimator into the beam monitor chamber from a dual energy linear accelerator," Journal of Medical Physics, vol. 32, No. 2, 2007 pp. 65-67.

Nomayr A et al.; 'MRI appearance of radiation-induced changes of normal cervical tissues', Eur Radiol., (2001), vol. 11, No. 9, doi:doi:10.1007/s003300000728, pp. 1807-1817, XP055095676.

Overweg et al. 'System for MRI guided Radiotherapy.' Proc. Intl. Soc. Mag. Reson. Med. 17(2009):594.

Papanikolaou, et. al., "Performance of dual layer micro MLC versus standard single layer MLC for IMRT delivery," Medical Physics, vol. 35, issue 6, 2008, p. 2746 (5 pages).

(56) References Cited

OTHER PUBLICATIONS

Partial International Search Report Issued in International Application No. PCT/US2013/039009, dated Oct. 18, 2013. 2 pages.
Pasternak et al., Free Water Elimination and Mapping from Diffusion, Magnetic Resonance in Medicine 62:717-730, 2009.
Patriciu, Alexandru, et al., 'Automatic Brachytherapy Seed Placement Under MRI Guidance'. IEEE Transactions on Biomedical Engineering. vol. 54, No. 8. Aug. 2007. pp. 1-8.
PCT App. No. PCT/US2010/039036; International Search Report dated Aug. 11, 2010; (pp. 1-2).
PCT App. No. PCT/US2010/042156; International Search Report and Written Opinion dated Sep. 10, 2010 ; 15 pages.
PCT App. No. PCT/US2016/063416; International Preliminary Report on Patentability and International Search Report with Written Option mailed Jun. 7, 2018; Attorney Docket No. 047176-0452638_525001WO. 9 pages.
PCT App. No. PCT/US2017/020015; International Search Report and Written Opinion dated Jul. 26, 2017; 18 pages.
PCT App. No. PCT/US2017/038867; International Search Report and Written Opinion dated Nov. 8, 2017; (pp. 1-12).
PCT App. No. PCT/US2017/066182; International Preliminary Report on Patentability dated Jun. 27, 2019; 8 pages.
PCT App. No. PCT/US2017/066182; International Search Report and Written Opinion dated Mar. 12, 2018; 22 pages.
Raaijmakers, A.J.E et al. 'Integrating a MRI scanner with a 6 MV radiotherapy accelerator: dose increase at tissue-air interfaces in a lateral magnetic field due to returning electrons.' Phys. Med. Biol. 50 (2005) pp. 1363-1376.
Raaymakers, B.W. et al. 'Integrating a MRI scanner with a 6 MV radiotherapy accelerator: dose deposition in a transverse magnetic field', Phys. Med. Biol. 49 (2004) 4109-4118.
Rancati et al., NTCP Modeling of Subacute/Late Laryngeal Edema Scored by Fiberoptic Examination, Int. J. Radiation Oncology Biol. Rhys., vol. 75, No. 3, pp. 915-923, 2009.
Reddy, B. Srinivasa, and B. N. Chatterji. 'An FFT-Based Technique for Translation, Rotation, and Scale-Invariant Image Registration.' IEEE Transactions on Image Processing, vol. 5, No. 8, Aug. 1996, pp. 1266-1271.
Reena, et. al, "Performance characterization of Siemens Primus linear accelerator under small monitor unit and small segments for the implementation of step-and-shoot intensity-modulated radiotherapy," Journal of Medical Physics, vol. 31, No. 4, 2006 pp. 269-274.
Riek, et al. "Flow Compensation in MRI Using a Phase-Corrected Real Reconstruction", Magnetic Resonance in Medicine 30, pp. 724-731, 1993.
Roullot Elodie et al. 'Regularized reconstruction of 3D high-resolution magnetic resonance images from acquisitions of anisotropically degraded resolutions.' Pattern Recognition, 2000. Proceedings. 15th International Conference on Sep. 3-7, 2000; [Proceedings of the International Conference on Pattern Recognition. (ICPR)], Los Alamitos, CA, USA, IEEE Comput. Soc, US, vol. 3, Sep. 3, 2000 (Sep. 3, 2000), pp. 346-349.
Sanguineti et al., Dosimetric Predictors of Laryngeal Edema, Int. J. Radiation Oncology Biol. Phys., vol. 68, No. 3, pp. 741-749, 2007.
Schlegel, et al., "New Technology in Radiation Oncology," Springer Berlin Heidelberg, New York, 2006 15 pages.
Schreiner, John; Kerr, Andrew; Salomons, Greg; Dyck, Christine, and Hajdok, George, 'The Potential for Image Guided Radiation Therapy with Cobalt-60 Tomotherapy', MICCAI 2003, LNCS 2879, pp. 449-456, 2003.
Schreiner, L. John, et al. 'The role of Cobalt-60 in modern radiation therapy: Dose delivery and image guidance'. Journal of Medical Physics, vol. 34, No. 3, 2009, 133-136.
Sempau, Josep et al. 'DPM, a fast, accurate Monte Carlo code optimized for photon and electron radiotherapy treatment planning dose calculations.' Phys. Med. Biol. 45 (2000) pp. 2263-2291, Received Feb. 29, 2000. Printed in the UK.
Sherouse, George W. et al. 'Virtual Simulation in the Clinical Setting: Some Practical Considerations', Int. J. Radiation Oncology Biol. Phys. vol. 19, pp. 1059-1065, Apr. 26, 1990, Pergamon Press, USA.
Siemens 160 MLC Multileaf Collimator Brochure, www.siemens.com/healthcare, Copyright Aug. 2010, 11 pages.
Siemens 3-D MLC and Optifocus Brochure, Siemens medical, www.siemens.com/medical, Oct. 2006, 2 pages.
Siemens Oncor Digital Medical Linear Accelerator Specifications Brochure 2009, Siemens, www.siemens.com/healthcare, 28 pages.
Siemens Oncor Linear Accelertor Brochure 2006, Siemens medical, www.siemens.com/medical, 11 pages.
Siemens, ModuLeaf Mini Multileaf Collimator Brochure, Siemens Medical, Copyright Feb. 2006, 8 pages.
Siochi, "Leakage reduction for the Siemens ModuLeaf," Journal of Applied Clinical Medical Physics, vol. 10, No. 2, Spring 2009, pp. 139-149.
St. Aubin et al,, 'Magnetic decoupling on the linac in a low field biplanar linac-MR system', Med. Phys, 37 (9), Sep. 2010, pp. 4755-4761.
Stoianovici, Dan, et al. MRI Stealth Robot for Prostate Interventions. Minimally Invasive Therapy. 2007. pp. 241-248.
Tacke, et al., "6 MV dosimetric characterization of the 160 MLC™, the new Siemens multileaf collimator," Medical Physics, vol. 35, No. 5, May 2008, pp. 1634-1642.
Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.
Tokuda, J. et al. 'Real-Time Organ Motion Tracking and Fast Image Registration System for MRI-Guided Surgery.' Systems and Computers in Japan Scripta Technica USA. vol. 37, No. 1. Jan. 2006: 83-92. Database Inspec [Online]. The Institution of Electrical Engineers, Stevenage, GB; Jan. 2006.
Tokuda, Junichi; Morikawa, Shigehiro; Dohi, Takeyoshi; Hata, Nobuhiko; Motion Tracking in MR-Guided Liver Therapy by Using Navigator Echoes and Projection Profile Matching, 2004. vol. 11. No. 1. pp. 111-120.
Topolnjak, "The six-bank multi-leaf system," Jun. 30, 2007, 119 pages.
Trzasko et al. 'Highly Undersampled Magnetic Resonance Image Reconstruction via Homotopic L0—Minimization' IEEE Transactions on Medical Imaging. vol 28. No. 1. Jan. 31, 2009, pp. 106-121.
Wang et al., Evolution of Radiation-Induced Brain Injury: MRI Imaging—Based Study, Radiology: vol. 254: No. 1; Jan. 2010.
Warrington, Jim et al. 'Cobalt 60 Teletherapy for Cancer: a Revived Treatment Modality for the 21st Century', 2002 The Institution of Electrical Engineers, pp. 19-1-19/19.
Wazer, David E. et al. 'Principles and Practice of Radiation Oncology (fifth edition).', Wolters Kluwer/Lippincott Williams & Wilkins. 2008. 2 pages.
Weaver, John B.; "Simultaneous Multislice Acquisition of MR Images", Magnetic Resonance in Medicine, John Wiley & Sons, Inc., vol. 8, No. 3, Nov. 1, 1988, pp. 275-284, XP000003030, ISSN: 0740-3194.
Webb, S. 'The physical basis of IMRT and inverse planning' The British Journal of Radiology, 76 (2003), 678-689, 2003 The British Institute of Radiology.
Webb, Steve, 'Intensity-modulated radiation therapy using only jaws and a mask: II. a simplified concept of relocatable single-bixel attenuators', published May 22, 2002, Institute of Physics Publishing, Physics in Medicine and Biology, Phys. Med. Biol. 47 (2002) 1869-1879.
Webb, Steve. "Historical Perspective on IMRT." Institute of Cancer Research and Royal Marsden NHS Trust. 2002. (23 pages).
Wljesooriya, et. al., "Determination of maximum leaf velocity and acceleration of a dynamic multileaf collimator: Implications for 4D radiotherapy," Medical Physics, vol. 32, No. 4, Apr. 2005, pp. 932-941.
Yang, Junfeng, et. al. 'A Fast TVL1-L2 Minimization Algorithm for Signal Reconstruction from Rartial Fourier Data.' Technical Report, TR08-27, CAAM, Rice University Houston, TX, 2008. pp. 1-10.

(56) References Cited

OTHER PUBLICATIONS

Zaitsev M et al.: "Shared k-space Echo Planar Imaging with Keyhole," Magnetic Resonance in Medicine, John Wiley & Sons, Inc. US, vol. 45, Jan. 1, 2001, pp. 109-117, XP002311925, ISSN: 0740-3194.

Zhu, et al., "Geometric and dosimetric analysis of multileaf collimation conformity," Radiotherapy and Oncology 47 (1998) pp. 63-68.

Zitova B et al, 'Image Registration Methods: a Survey', Image and Vision Computing, Elsevier, Guildford, GB, (Oct. 1, 2003), vol. 21, No. 11, doi:10.1016/S0262-8856(03)00137-9, ISSN 0262-8856, pp. 977-1000, XP001189327.

Japanese Office Action, Application No. 2019-531172, dated Sep. 7, 2021.

\* cited by examiner

RADIATION THERAPY SYSTEMS AND METHODS

CROSS-REFERENCE TO RELATED APPLICATION

This application is a continuation of U.S. patent application Ser. No. 15/840,941, filed Dec. 13, 2017, titled Radiation Therapy Systems and Methods, which claims the benefit of U.S. Provisional Application No. 62/433,745, filed Dec. 13, 2016, titled "Radiation Therapy Systems And Methods," the disclosures of which are hereby incorporated by reference.

BACKGROUND

The present disclosure relates to systems, methods and computer software for performing radiation therapy, including the collimating or shaping of a radiation beam. Collimators may be used, for example, to shape a radiation beam for the purpose of providing precise medical radiation therapy. Radiation therapy systems, methods and software may also incorporate imaging, for example, CT imaging may be performed prior to the delivery of radiation therapy or MRI imaging may be performed during the delivery of radiation therapy.

SUMMARY

Systems, methods and software related to performing radiation therapy are disclosed. Some implementations may include a diagnostic-quality CT scanner for imaging a patient, with the diagnostic-quality CT scanner having an imaging isocenter. Such implementations may also include a radiation therapy device positioned adjacent the diagnostic-quality CT scanner. The radiation therapy device may include a gantry carrying a radiation therapy beam source and having a radiation therapy isocenter separate from the imaging isocenter of the diagnostic-quality CT scanner. Also, a couch may be configured to position the patient for imaging and for radiation therapy by translating the patient between the diagnostic quality CT scanner and the radiation therapy device. Some implementations may include the system being configured to deliver only co-planar radiation therapy.

In some variations, the radiation therapy device may be not cantilevered. The gantry may be a ring gantry and may be configured to move the source only to different positions within a plane. Also, the couch may be configured to not rotate.

In some variations, the radiation therapy beam source may be a linear accelerator and the linear accelerator may be divided into components spaced around the gantry and utilize at least one RF waveguide between the linear accelerator components.

In some variations, the diagnostic-quality CT scanner may be designed for RT simulation, or may be a PET/CT scanner.

In some implementations, the system may include a control system configured to utilize diagnostic-quality CT images to reoptimize a treatment plan. Reoptimization may be performed just prior to treatment, while the patient is on the couch.

In certain implementations, the gantry may be configured to be translated orthogonally to couch motion. Also, the gantry may be configured to be translated over a range of at least 8 cm to facilitate the positioning of the radiation therapy isocenter in the patient before treatment.

In yet other implementations, the system may further include a collimating system for collimating the radiation beam. The collimating system may have a first multileaf collimator having a plurality of leaves and a second multileaf collimator having a plurality of leaves and be configured such that the radiation beam will pass through the first multileaf collimator before passing through the second multileaf collimator, and pass through the second multileaf collimator before hitting the target.

In some implementations, the leaves of the first multileaf collimator and the leaves of the second multileaf collimator may be configured to move independently of one another. At least one of the first multileaf collimator and the second multileaf collimator may be double focused.

In certain implementations, the first multileaf collimator may have a focus point and the second multileaf collimator may have a focus point and the focus point of the first multileaf collimator may be different from the focus point of the second multileaf collimator. The differing focus points of the first multileaf collimator and the second multileaf collimator may improve the match of penumbra between the first multileaf collimator and the second multileaf collimator. The focus point of the first multileaf collimator may also be at the effective source point and the focus point of the second multileaf collimator may be moved off of the effective source point.

The first multileaf collimator and second multileaf collimator may be further configured to collimate a beam thinner than the widths of the leaves of the first and second multileaf collimators. The leaves of the first multileaf collimator may also be configured to be immediately adjacent one another and the leaves of the second multileaf collimator may also be immediately adjacent to one another.

In yet other implementations, the system may further include radiation shielding between the radiation therapy device and the diagnostic-quality CT scanner. The radiation shielding may include a high atomic number material covering or replacing a portion of an outer shroud of the diagnostic quality CT scanner facing the radiation therapy device.

In some implementations, the radiation therapy device may be a linac and the system may further include RF shielding for at least one component of the linac.

In other implementations, the system may include at least one versatile baseplate configured to mount at least one system selected from a group comprising a radiation therapy device, a CT scanner, an MRI, a CT couch, a PET/CT couch, and an MRI couch. The at least one versatile baseplate may allow the system to be converted between CT guidance and MRI guidance without removing the radiation therapy device.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
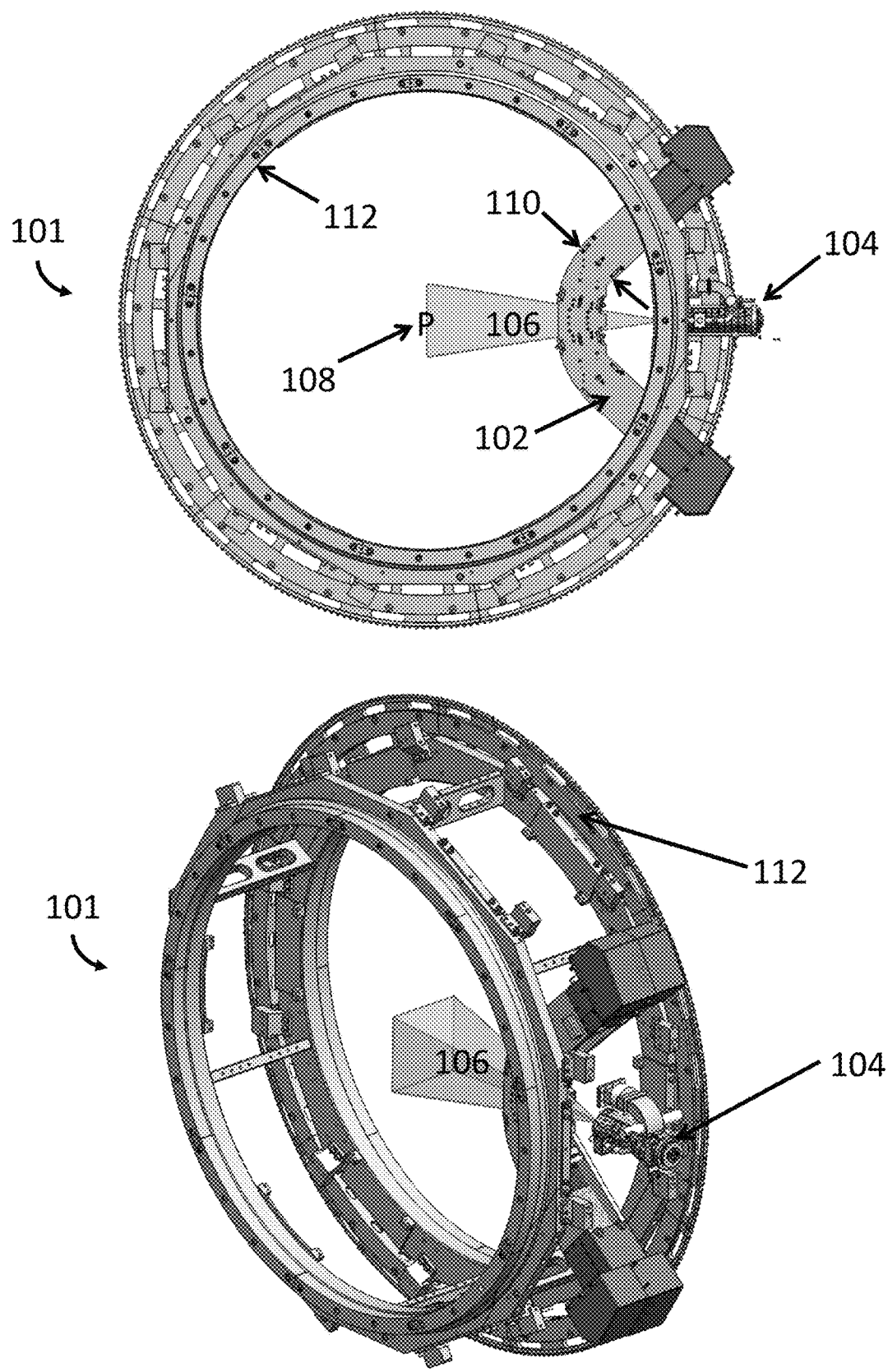
FIG. 1 is a simplified diagram illustrating an exemplary radiation therapy device utilizing an exemplary gantry and a collimating device with a radiation source in accordance with certain aspects of the present disclosure.

An exemplary radiation therapy device 101 is depicted in FIG. 1 including a gantry 112 carrying a radiation source 104 capable of emitting a radiation beam 106.

A collimating device 102 may be placed in the path of radiation beam 106 and configured to selectively attenuate radiation beam 106 as it travels toward a target 108. The radiation source 104 may be, for example, a radioisotope, a heavy ion accelerator, a linear accelerator for producing an electron or photon beam, or the like. While the technology of the present disclosure may be used in any field where radiation beams are utilized, an embodiment described herein depicts a medical patient P as target 108.

Figure 2:
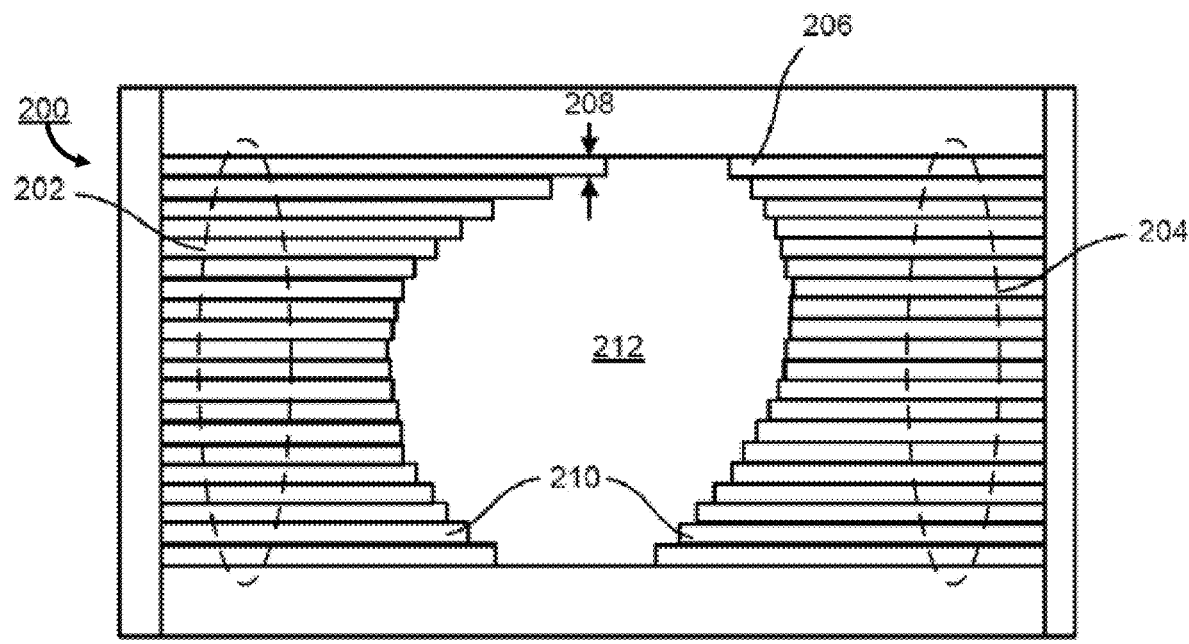
FIG. 2 is a simplified illustration of an exemplary multi-leaf collimator and the manner in which it can create an aperture in accordance with certain aspects of the present disclosure.

FIG. 2 depicts a particular type of collimating device known as a Multi-Leaf Collimator (or MLC). The exemplary MLC 200 shown includes a bank of movable leaves 202 opposite a second bank of movable leaves 204. In such a device, each leaf 206 is independently adjustable in order to enable the forming of an aperture 212, which collimates the beam into the desired shape for treatment.

Each leaf in MLC 200 may be described as having a width 208 and a height 110 (height is shown in FIG. 1). The height 110 may also be described as the "thickness" of a leaf and is important in determining the amount of attenuation of beam 106 by MLC 200. The amount of attenuation is also affected by the material that the leaves of the MLC are made of and therefore high-attenuating materials are used such as tungsten, tungsten alloys, tantalum, tantalum alloys, lead, lead alloys and the like.

Figure 3:
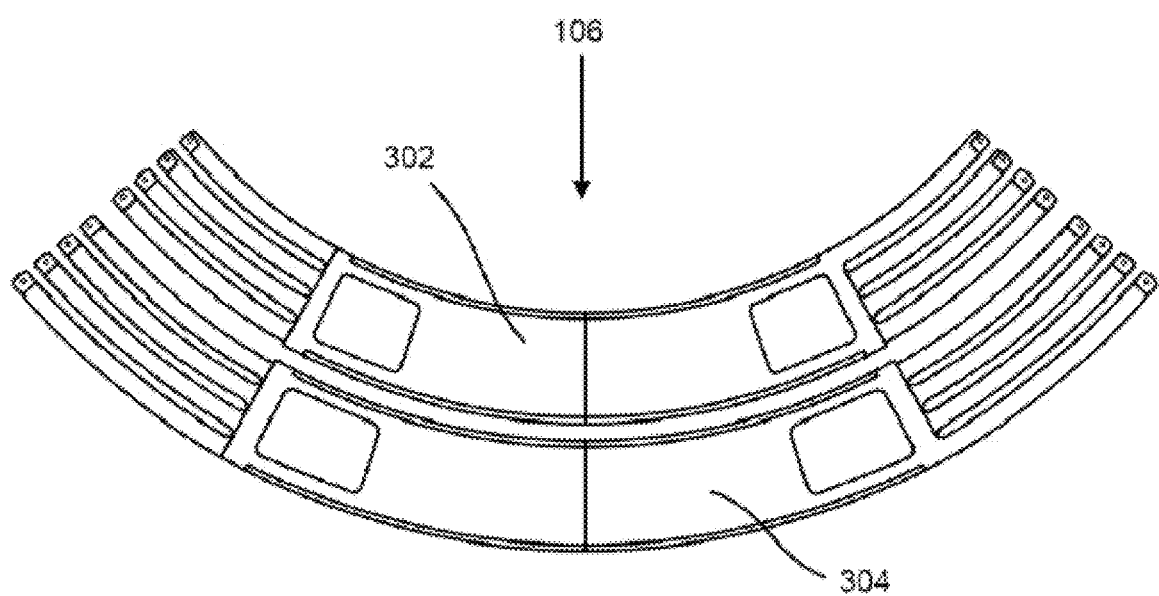
FIG. 3 is a simplified illustration of an exemplary double-stacked collimating device in accordance with certain aspects of the present disclosure.

An exemplary collimating system contemplated by the present disclosure is depicted in FIG. 3 and comprises multiple "stacked" MLCs. For example, the embodiment depicted includes a first MLC 302 and a second MLC 304. The MLCs are stacked such that their attenuation values are additive with respect to radiation beam 106. The first MLC 302 is positioned closer to radiation source 104 than second MLC 304, so that radiation beam 106 passes through first MLC 302 before passing through second MLC 304. The embodiments depicted herein show two stacked MLCs but it is contemplated that additional MLCs could be added (e.g., a stack of three) following the general teachings of the present disclosure.

While it is common for collimating devices to be placed close to radiation source 104, the present disclosure contemplates an embodiment that moves the collimating device closer to the target or patient. For example, a preferred implementation of the present disclosure moves the collimating device as close to the target as possible, without restricting the desired bore or volume to be occupied by the target/patient. In one preferred implementation, the edge of the collimating device closest to target 108 (i.e., the edge of the second MLC 304 that is farthest from radiation source 104) is less than 60 cm from isocenter, and preferably about 50 cm from isocenter. It is contemplated that such a design facilitates positioning of the collimating device during assembly and decreases beam penumbra.

Figure 4A:
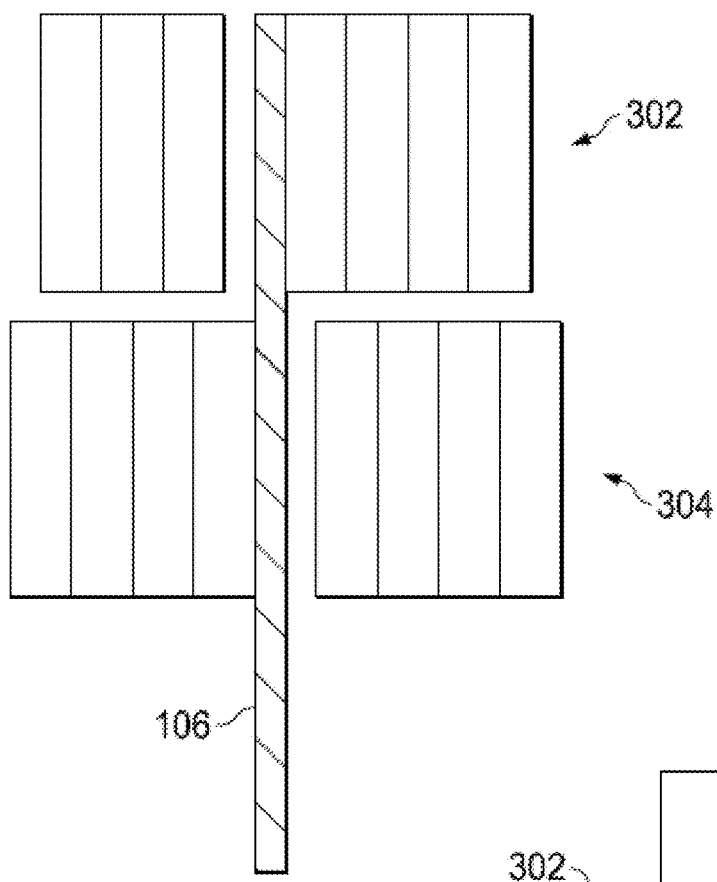
FIGS. 4A and 4B are simplified illustrations of a manner in which a double stacked collimating device may collimate a radiation beam in accordance with certain aspects of the present disclosure.
Figure 4B:
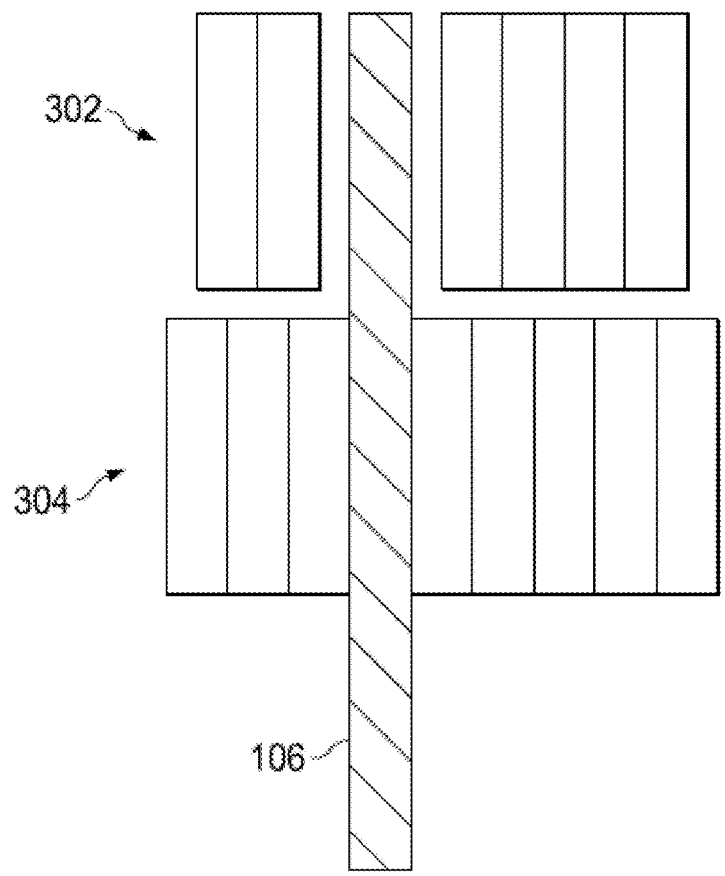

FIG. 4A and FIG. 4B are simplified illustrations of how beams may be collimated with an exemplary double-stacked MLC system. As shown in both figures, the leaves in the first MLC 302 and second MLC 304 are offset by one half the width of the leaves, or by approximately one half of the width of the leaves. The leaves in first MLC 302 and second MLC 304 can be moved independently of one another. In FIG. 4A, one leaf in first MLC 302 and one leaf in second MLC 304 can be retracted to create the smallest aperture through which beam 106 may pass (in the dimension corresponding to the width of the leaves). As a result, the leaves of the MLCs are offset in a manner to allow for collimation of a beam thinner than the widths of the leaves of each of the first and second multileaf collimators.

In one particular implementation, the width of such a beam may be 4.15 mm when the width of the leaves in both first MLC 302 and second MLC 304 are approximately 8.3 mm. FIG. 4B shows that when two leaves of one of the MLCs are retracted and an overlapping leaf in the other MLC is retracted, the second smallest aperture through which radiation beam 106 may pass is created, for example, a beam having a width of 8.3 mm.

In one implementation, the MLCs are stacked, the leaves in each MLC are approximately the same width, and the leaves in first MLC 302 are offset from the leaves in second MLC 304 by approximately one-half of their width (as shown in FIG. 4). The MLC leaves in such an implementation may be designed to be approximately twice the width of a typical MLC, while still achieving approximately the same resolution. For example, to achieve a 5 mm resolution at isocenter, a typical single MLC will require leaves approximately 2.5 mm wide, while in a double-stacked design with offset, the leaves may be approximately 5 mm wide and achieve the same resolution. Such a design may be desirable for ease of machining and to provide more material for equipment connecting to or interfacing with the leaves.

Figure 5:
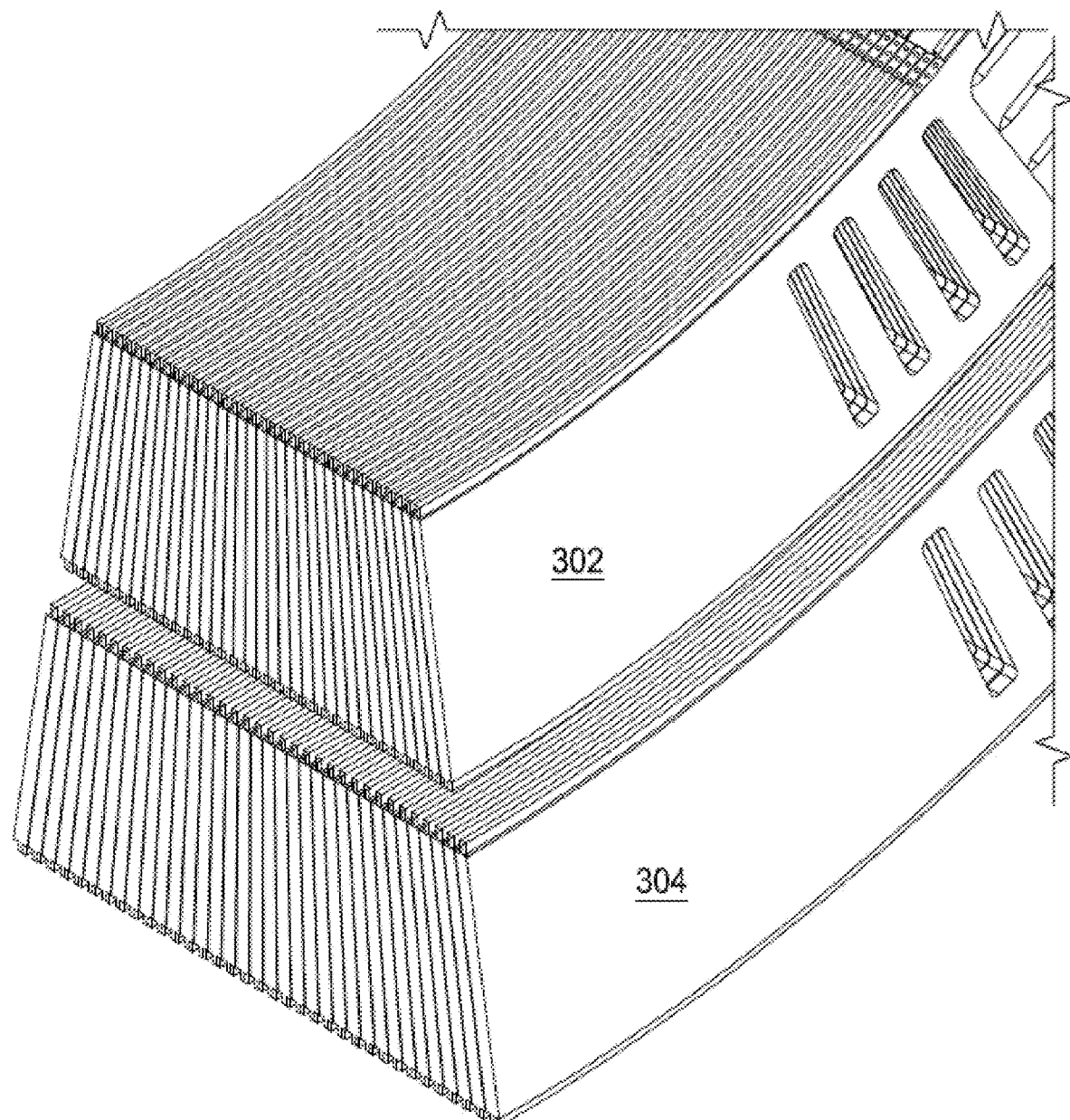
FIG. 5 is a simplified isometric illustration of an exemplary double-stacked collimating device in accordance with certain aspects of the present disclosure.

FIG. 5 is an isometric view of the exemplary collimating system of FIG. 3 showing double stacked MLCs 302 and 304. Because the exemplary collimating system includes multiple MLCs, arranged to have an additive beam attenuating affect, the leaves in each of the individual MLCs may have a decreased height, or thickness, compared to the leaves in a standard single MLC collimating system. As an example, where two MLCs are utilized, the leaves in each MLC may be approximately one half the height of the leaves in a typical single MLC made of the same material. Such may decrease the weight of individual leaves, making them easier to control and allowing for more rapid movement, which can reduce overall treatment time. Moreover, if the collimators are designed to be focused or double focused (as preferred, and described further below), the edges of the MLCs exposed to the beam will have greater attenuation and the leaves of each of the MLCs may be further decreased in height.

Given the beam collimating features shown in FIG. 4, and the importance of beam attenuation described herein, preferred implementations of the present disclosure utilize leaf heights for first MLC 302 and second MLC 304 that are the same, or approximately the same. Because both the first MLC 302 and second MLC 304 are responsible for shaping radiation beam 106, both first MLC 302 and second MLC 304 are each preferably designed with leaf heights sufficient to fully attenuate the radiation beam 106, as an example, for medical radiation therapy. In one particular implementation, the leaves of both first MLC 302 and second MLC 304 are made with a tungsten alloy of 17.5 gm/cc or higher density (e.g., 5:5:90 Cu:Ni:W) and are each approximately 5.5 cm thick. A preferred exemplary collimating system may include 34 leaves in each bank of the first MLC 302, and 35 leaves in each bank of the second MLC 304, although different resolutions and numbers of leaves in each bank are contemplated.

It is preferable that the MLCs used with the technology of the present disclosure be double focused, as shown in the drawings (as opposed to using non-focused collimators such as those having linear leaf motion and rounded leaf ends). MLCs are double focused when all of the beam defining surfaces of the leaves project back to the radiation source. For example, with reference to FIG. 1, radiation beam 106 fans out from radiation source 104. Because the exemplary collimating systems utilize curved leaves that retract along an arc (e.g., as shown in FIGS. 1, 3), the edges of the leaves, as they retract, always represent a line projecting back to radiation source 104. With such a design, the entire thickness of the leaves will attenuate beam 106 as it passes through the collimating device, providing for a sharper beam edge with low penumbra regardless of how far the leaves are retracted.

Figure 6:
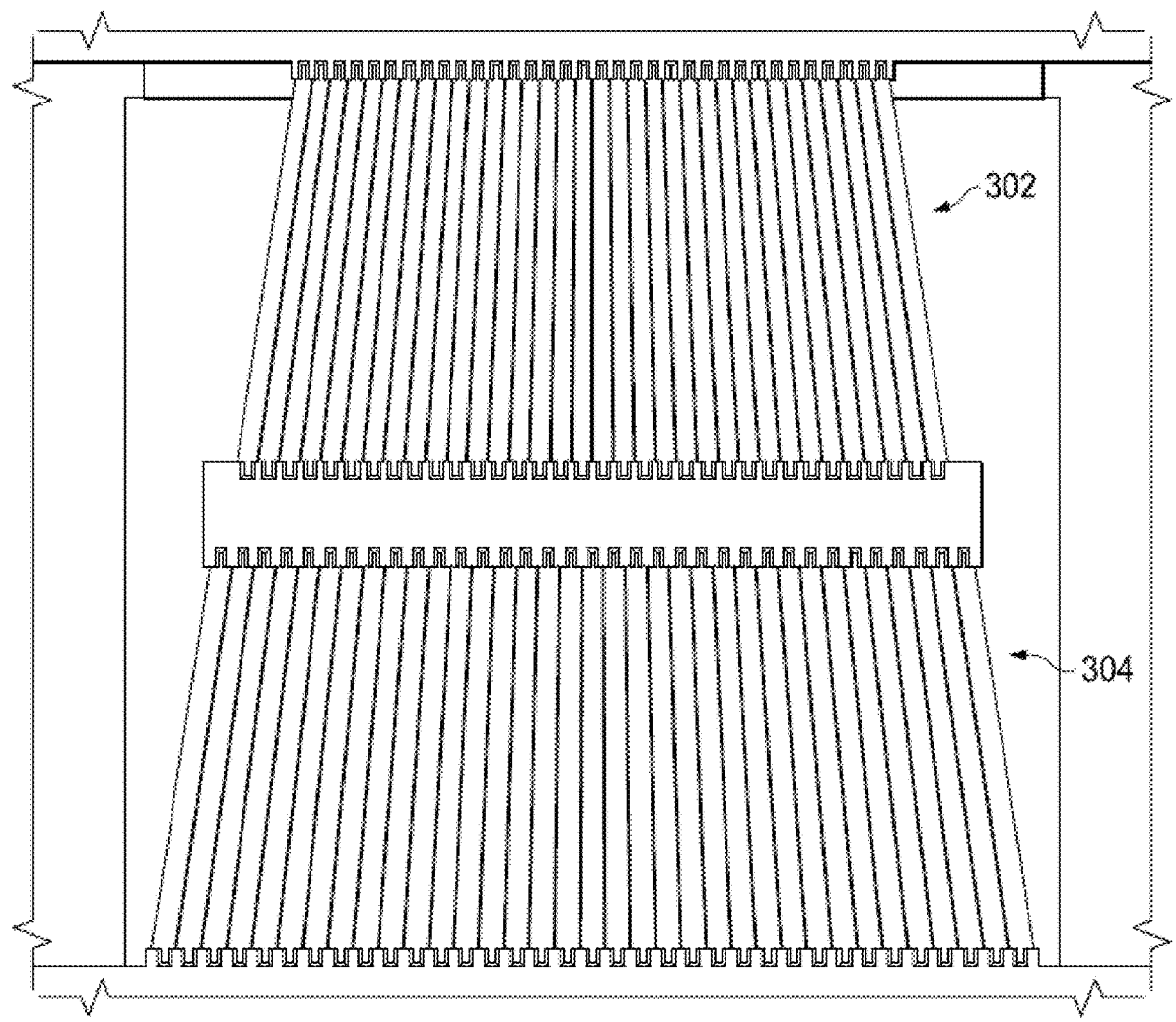
FIG. 6 is a simplified illustration of an exemplary double-stacked collimating device in accordance with certain aspects of the present disclosure.

When all four of the leaf surfaces that collimate beam 106 project back to the radiation source, the collimating system is "double" focused. FIG. 5 illustrates a manner by which the MLCs may focus beam 106 in the other dimension—by virtue of the leaves' width increasing with distance from radiation source 104. In FIG. 5, for example, the width of the leaves at the top of MLC 302 is the thinnest. The width is larger at the bottom of the leaves of MLC 302, larger still at the top of the leaves in second MLC 304, and largest at the bottom of the leaves in MLC 304. This design is also illustrated in FIG. 6.

In one implementation, the focusing of the leaf designs is purposefully defocused slightly. For example, the leaf surfaces may designed to project to a point one to two centimeters above or below the actual radiation source. This slight defocusing can significantly decrease radiation leakage through the space between the leaves (i.e., interleaf gaps), while having only a small impact on beam penumbra.

In another implementation, first MLC 302 and second MLC 304 have different focus points. The arcs on which the MLCs travel would therefore intersect at some point but within their boundaries they can be designed to have sufficient clearance from one another. The differing focus points may be chosen to improve the match of penumbra between the first multileaf collimator and the second multileaf collimator even though they are at different distances from the source. For example, the focus of the first MLC can be placed at the effective source point and the focus of the second MLC can be moved off of the effective source point. Such an exemplary design would increase the penumbra of the lower MLC to better match the penumbra of the upper MLC and provide better dosimetric matching of the beam edges shaped by first MLC and second MLC.

With conventional, non-focused MLCs, collimator jaws are necessary to prevent radiation leakage outside of beam apertures. As the rounded leaf ends of a conventional MLC are poor at blocking radiation even when completely closed, closed leaf ends are often moved to a position where they are blocked by the conventional collimator jaws. The utilization of double focused leaves limits leaf end leakage and penumbra to an extent that an adjacent, stacked MLC of reasonable thickness (having an offset leaf-meeting location) will be sufficient to block transmission so that conventional collimator jaws are not necessary. The present disclosure thus contemplates collimating systems that do not include collimator jaws.

While preferred implementations of the present disclosure utilize double focused MLCs, it is contemplated that single focused or unfocused MLCs may also be utilized, or a mixture of focusing types may be used across multiple stacked MLCs.

When comparing the width of the leaves of first MLC 302 and second MLC 304 in a focused implementation, it is noted above that the leaf width continually increases with distance from radiation source 104. That being said, a preferred implementation of the present disclosure includes leaf designs with approximately the same width in the first MLC 302 as in the second MLC 304. When described in this way, "approximately the same width" means that the bottom width of the leaves in first MLC 302 is approximately the same (i.e., just slightly smaller) than the top width of the leaves in second MLC 304. Stated another way, focused leaves in the first and second MLCs can be thought of as having approximately the same width—including a small additional width being added along the leaves as they extend further from radiation source 104, as is necessary to provide a focused design (e.g., as shown in FIGS. 5 and 6).

While a preferred implementation utilizes leaf designs where leaf widths in first MLC 302 and second MLC 304 are approximately the same, the present disclosure contemplate designs where the leaf widths can be different between the stacked MLCs.

In a preferred implementation of the present disclosure, the leaves of first MLC 302 are immediately adjacent to each other or touching, and the leaves of second MLC 304 are immediately adjacent to one another or touching. In this implementation, the gaps between adjacent leaves in both first MLC 302 and second MLC 304 are minimized in a manner that will minimize radiation leakage between the leaves, yet still allow for relative motion. This type of implementation is illustrated in, for example, FIGS. 4, 5, and 6.

Because the leaves of an MLC are able to move independently, there is necessarily a small gap between them through which some radiation may pass. The collimating system of the present disclosure contemplates that the leaves of first MLC 302 and the leaves of second MLC 304 are preferably arranged so the gaps between leaves are not aligned so radiation beam 106 may not transmit through a leaf gap in first MLC 302 and then directly through a leaf gap in second MLC 304. Instead, the leaves of first MLC 302 are preferably offset from the leaves of second MLC 304 so that there is no straight-line path for the beam to travel through the inter-leaf gaps of both of MLCs. See, for example, FIGS. 4, 5 and 6.

In an exemplary embodiment, the leaves of first MLC 302 and second MLC 304 are offset by approximately 50% of their width so as to provide the greatest separation between the inter-leaf gaps of the first MLC 302 and the second MLC 304. Offsets of less than 50% of the leaf width are contemplated by the present disclosure but an offset is preferably utilized and is preferably is greater than 10% of the width of the leaves.

In typical collimating systems with only one MLC, interleaf leakage must be prevented through complex machining of the leaves in the location where they mate or abut one another. For example, tongue and groove or stepped designs may be employed to interrupt an otherwise linear inter-leaf gap that could allow significant beam leakage. The collimating system of the present disclosure contemplates the ability to eliminate such additional machining because, even if straight-edged leaves are utilized, the leakage path through the collimating system will be in interrupted by virtue of the previously described overlap or offset of the leaves between first MLC 302 and second MLC 304. A preferred implementation includes simple, straight-edged leaves without additional machining or features to block interleaf leakage. Such a design may also result in a more uniform leaf edge and decreased beam penumbra.

Figure 7:
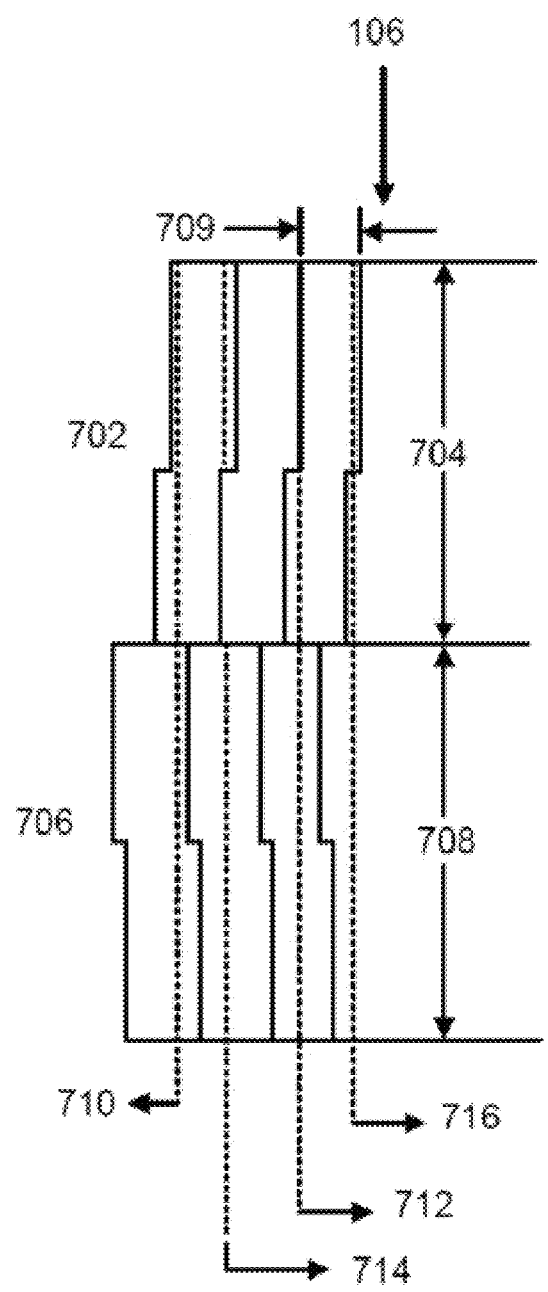
FIG. 7 is a simplified illustration of an exemplary double-stacked collimating device utilizing stepped leaf designs in accordance with certain aspects of the present disclosure.

In an alternative embodiment of the presently described collimating system, despite having multiple MLCs and leaf offsets, the mating surfaces of the leaves may be machined to further decrease the leakage paths and enable reduction of the height of the MLCs. Any configuration of nonlinear surfaces may prove beneficial, such as a tongue and groove design, or the like. In an exemplary embodiment, depicted in FIG. 7, steps are machined into the mating surfaces of the leaves. FIG. 7 shows a first partial leaf bank 702, corresponding to first MLC 302 and second partial leaf bank 706, corresponding to second MLC 304. In the depicted embodiment, the leaves have a width 709 and heights 704 and 708. In an exemplary embodiment, leaf height 704 of partial leaf bank 702 and leaf height 708 of partial leaf bank 706 are the same and are approximately 5.5 cm. It is not necessary, however, for the height of each of the leaf banks to be the same.

The exemplary leaf mating surface machining depicted in FIG. 7 is a step feature, included in the leaves of both the first MLC 302 and second MLC 304. For the purposes of simplified discussion we will assume that height 704 and height 708 are the same, and both equal to the variable "H". In the example of FIG. 7, there will exist transmission paths such as path 710, where the incident radiation beam 106 must travel through the full height 704 of leaf bank 702, and the full height 708 of leaf bank 706, exhibiting maximum beam attenuation through a thickness of 2×H. However, there are also transmission paths that will encounter interleaf gaps, such as paths 712 and 714, which will exhibit decreased attenuation as a result of only passing through a total leaf thickness of H+½ H=3⁄2 H. Nevertheless, this attenuation thickness of 3⁄2 H is greater than the thickness of only 1 H that would be encountered in a double stacked collimating system without the "step" feature. The step feature thus allows for a 33% reduction in the total height of the leaves in MLC 302 and MLC 304 to achieve the same attenuation observed by MLCs without the step feature. Such a feature may therefore be used to reduce the amount of material required and the weight of the leaves, thereby improving MLC speed and performance. As an example, the leaf height for each of the MLCs 302 304 may be approximately 3.7 cm.

In a double-stacked design, with offset, the leaf offset will result in beam 106 being attenuated by only about half of the typical amount of material at locations at the edge of aperture 212. Or, if a step feature is utilized, radiation beam 106 will be attenuated by even less material (see, for example, path 716 in FIG. 7).

Figure 8:
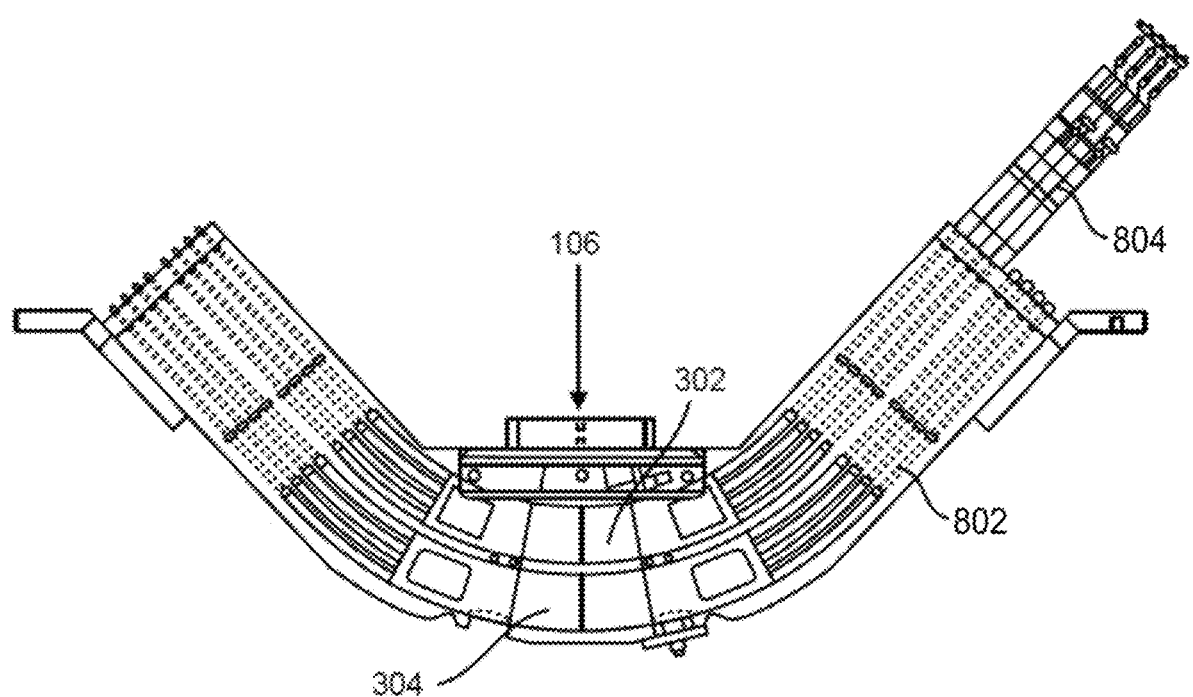
FIG. 8 is a simplified illustration of an exemplary double-stacked collimating device with additional drive hardware in accordance with certain aspects of the present disclosure.

The exemplary MLC assemblies discussed herein may also include mechanical structures for supporting and driving the leaves, servomotors for manipulating the position of the leaves, and control systems for achieving the desired beam shape and attenuation. FIG. 8 is a further depiction of the exemplary collimating system, with the inclusion of drive linkages 802 and leaf drive motor assemblies 804. A number of other related systems such as control systems, encoders, power cables, etc., are not depicted but may also be included.

Figure 9:
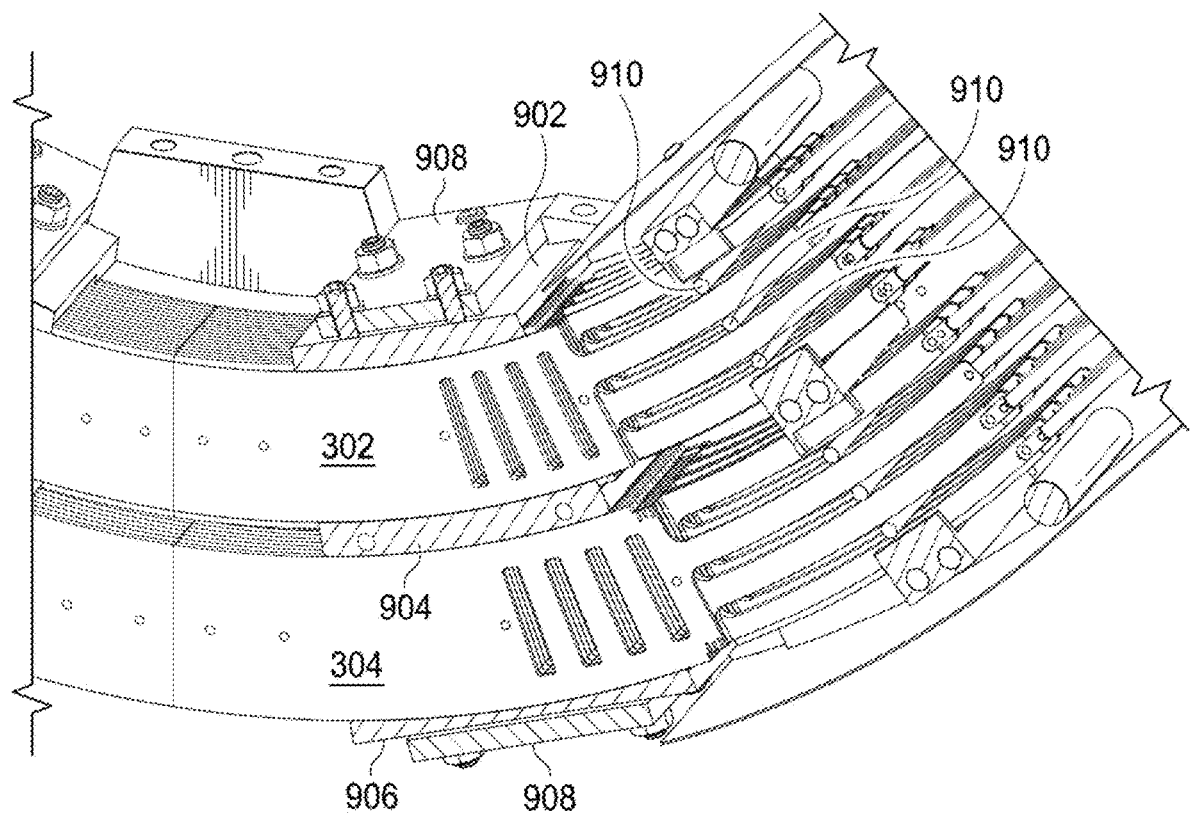
FIG. 9 is a simplified illustration of an exemplary double-stacked collimating device with additional guide hardware in accordance with certain aspects of the present disclosure.

FIG. 9 depicts additional structures for supporting and driving the leaves of an exemplary collimating system including a top leaf support guide 902, a middle leaf support guide 904, and a bottom leaf support guide 906. In one embodiment, the leaves include tabs at their top and bottom surfaces, which may ride within grooves in the leaf support guides (see, e.g., FIG. 6). In addition, guide pressure adjustment plates 908 may also be included to ensure smooth, but not loose, movement of the leaves. One particular implementation may also include rods 910 to further guide movement of the leaves and avoid excessive rocking.

Figure 10:
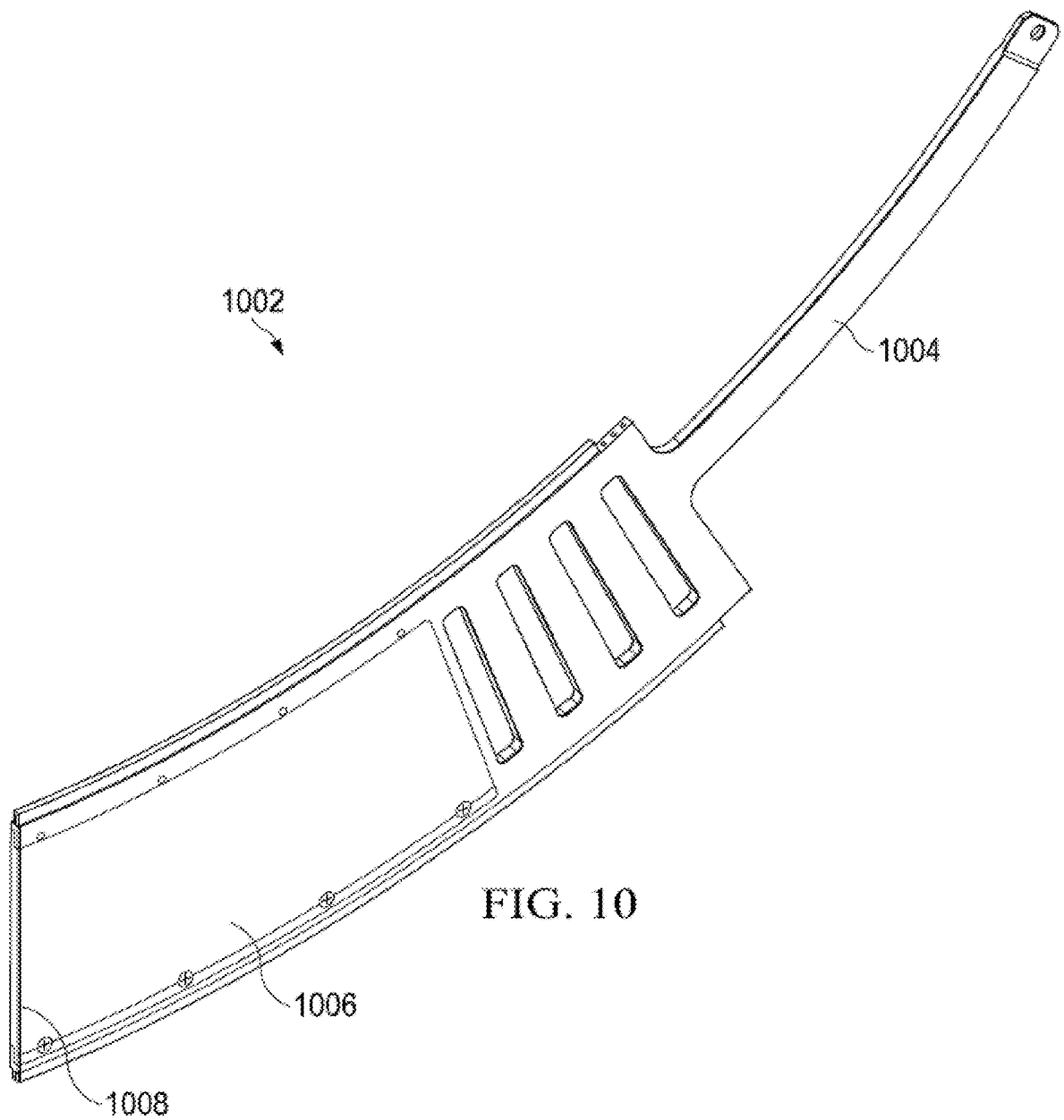
FIG. 10 is a simplified illustration of an exemplary leaf assembly in accordance with certain aspects of the present disclosure.

Referring now to FIG. 10, one implementation for the design of a leaf assembly 1002 utilizes a frame 1004, separate from attenuating material 1006. In such a design, the frame 1004 portion of leaf assembly 1002 that will engage with leaf support guides can be made with a material different from that of attenuating material 1006. While the attenuating material 1006 is typically a tungsten alloy or other high density material for radiation attenuation, the frame 1004 may be made from another material, for example, stainless steel. Attenuating material 1006 may be designed to be an insert into frame 1004 and the two materials may be fixed together using a number of methods such as bonding, sintering or welding. Preferably, frame 1004 does not extend all the way to the attenuating edge 1008 of leaf assembly 1002 to avoid variation in the overall attenuating properties of the leaf assembly 1002.

Figure 11:
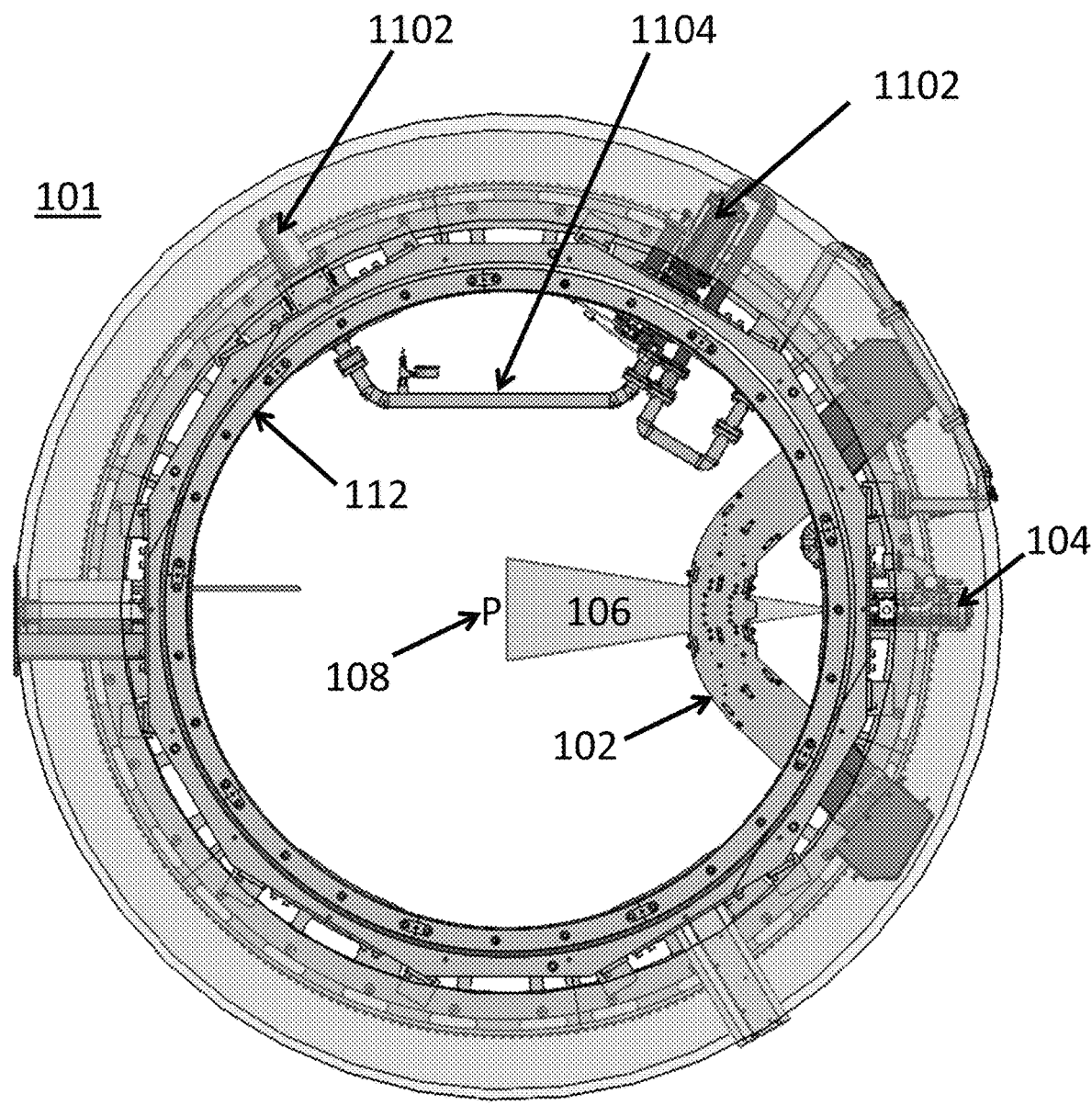
FIG. 11 is a simplified illustration of an exemplary radiation therapy device where a linear accelerator is divided into components spaced around the gantry in accordance with certain aspects of the present disclosure.

As described above with respect to FIG. 1, an exemplary radiation therapy device 101 may utilize a gantry 112 carrying a radiation source 104 capable of emitting a radiation beam 106. FIG. 11 depicts an implementation of radiation therapy device 101 where the radiation source 104 is a linear accelerator and the linear accelerator is divided into components 1102 spaced around gantry 112. Such a configuration may utilize RF waveguides 1104 between the linac components 1102 and can result in an overall decrease to the maximum diameter of radiation therapy device 101. In an alternative implementation, multiple radiation sources may be included around gantry 112.

An exemplary gantry 112 is as compact as possible while having a large bore, for example, the bore may be designed to be greater than 80 cm. In one implementation the bore is 110 cm.

One implementation of a gantry contemplated herein is a ring gantry, which may carry at least one radiation therapy beam source and be used to reorient the beam source during therapy in a manner allowing for the delivery of coplanar beams. When the term ring gantry is used herein, it is contemplated that the gantry not necessarily need to be purely in the shape of a ring. Gantries that deviate from a circular shape, or that even incorporate break(s) in their structure are contemplated.

The radiation therapy devices discussed herein may utilize any of the beneficial collimating device embodiments and concepts described above. Such devices will have very little transmission, low-penumbra beams, and be capable of delivering high-quality treatment plans. As a result, the present disclosure contemplates embodiments of radiation therapy systems that are configured to deliver only coplanar radiation therapy. For example, while radiation therapy devices disclosed herein may be configured to position beam source(s) in ways that allow non-coplanar therapy, or to translate a patient couch while a beam is on (e.g., the helical delivery of TomoTherapy), certain implementations will alternatively be configured to move beam source(s) only to different positions within a single plane and to deliver only coplanar radiation therapy. A ring gantry as depicted in FIGS. 1 and 11 may be utilized in such an implementation. In addition, while it is contemplated that a radiation therapy device of this disclosure may be cantilevered, and a couch associated with the radiation therapy device may be rotatable (to allow for non-coplanar therapy), in certain implementations the patient couch is not configured to rotate and the radiation therapy device is not cantilevered, yet the system can nevertheless deliver high-quality treatment plans. The term cantilevered, as used herein, refers to the inclusion of an arm or other structure to extend the location where the radiation beam emits from the device out away from the main rotating structure. Such cantilevered devices are typically used with couches that rotate to enable non-coplanar therapy to a patient from a beam source that only moves within a given plane. For a device to be "cantilevered" as it relates to the present disclosure, the location where the radiation beam is emitted must be extended substantially, e.g., for the purpose of allowing a couch to rotate and enable the delivery of non-coplanar beams. A radiation therapy device where the beam emission location is extended only a minor distance not sufficient for the enablement of non-coplanar therapy, is not considered cantilevered.

Embodiments of the radiation therapy devices disclosed herein may be used to perform arc therapy (also called VMAT), where the radiation therapy beam source emits a radiation beam while the source is moving (e.g., during rotation of a gantry). However, certain beneficial embodiments utilizing the collimating device concepts discussed above may be designed so that the radiation therapy device is not configured to deliver arc therapy, but can nevertheless deliver high-quality treatment plans in a short period of time.

The present disclosure contemplates the use of a diagnostic-quality CT scanner in conjunction with the disclosed radiation therapy systems. Diagnostic-quality CT scanners are typically continuously rotating CT systems, based on 'slip-ring technology' with single or multi-slice detector capabilities and capable of axial or helical data acquisition and image reconstruction. They can have multiple sources and detector arrays configured to acquire many tens to hundreds of image slices. They are often employed in diagnostic X-Ray departments of a hospital or clinic and typically utilize kilovoltage energy X-Rays in a fan beam geometry that rotates around the patient. Diagnostic quality CT scanners are often employed to acquire high quality CT imaging for use in the treatment planning of radiation therapy patients. The high quality CT images allow for the calibration of Hounsfield numbers to tissue density for improved dose computation.

Diagnostic quality CT scanners are distinct from cone beam CT systems that may employ a retractable X-Ray tube and flat panel imager to create cone beam X-Ray CT. The CT imaging data produced by a cone beam CT (a.k.a. CBCT) suffers from poorer image quality than standard CT units, lower soft tissue contrast, organ motion artifacts, and Hounsfield numbers that do not accurately reflect the electron density of the imaged tissues. Diagnostic-quality CT scanners are also distinct from megavoltage systems that may use the megavoltage radiation therapy beam as an imaging source, with a flat panel imager, to produce megavoltage CT images that also lead to poor quality noisy images with low soft tissue contrast.

Figure 12:
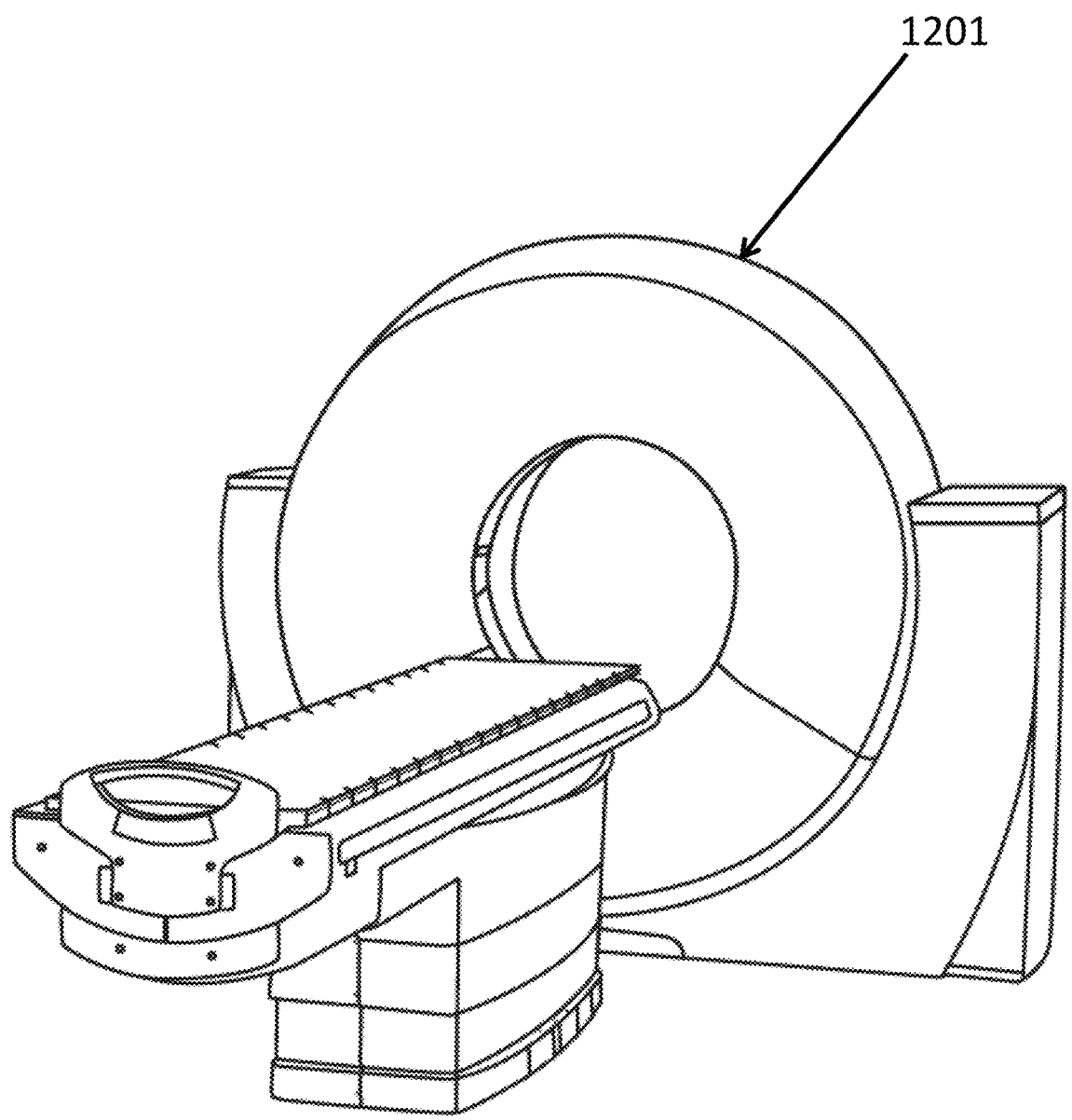
FIG. 12 is a simplified illustration of an exemplary "off-the-shelf" diagnostic-quality CT scanner designed for radiation therapy simulation in accordance with certain aspects of the present disclosure.

Certain implementations of diagnostic-quality CT scanners utilized herein will have a large bore (e.g., 70-90 cm). In one implementation, the diagnostic-quality CT scanner may be an "off-the-shelf" unit designed for radiation therapy simulation, including a couch compatible with radiation therapy and therapy immobilization equipment. One example of such a scanner 1201 is depicted in FIG. 12. Alternatively, the diagnostic-quality CT scanner may be a PET/CT scanner with a CT scanner adjacent a Positron Emission Tomography (PET) scanner.

A diagnostic-quality CT scanner may be placed adjacent to any of the radiation therapy devices discussed herein for the beneficial uses discussed below. In one implementation (depicted in FIG. 13), the CT scanner 1201 may be placed adjacent a radiation therapy device 101 utilizing a ring gantry, as previously discussed herein. "Adjacent" simply means in close proximity, and contemplates the devices touching, being separated slightly, or being integrated together. The CT and radiation therapy devices are, however, intended to have separate gantries in the preferred implementation.

In the combined CT/RT system, the diagnostic-quality CT scanner has an imaging isocenter and the radiation therapy device has a radiation therapy isocenter that is separate from the imaging isocenter. Separate is understood to mean that the isocenters are a significant distance apart, for example, such that a couch must move the patient between imaging and treatment. In one implementation, the isocenters are approximately 80 cm away from one another. In a preferred implementation, the CT scanner and radiation therapy device are fixed in position relative to one another, and also relative to the treatment room, meaning that they are mounted in a way that they cannot be moved (as if, for example, they were on rails, or a turntable).

Figure 13:
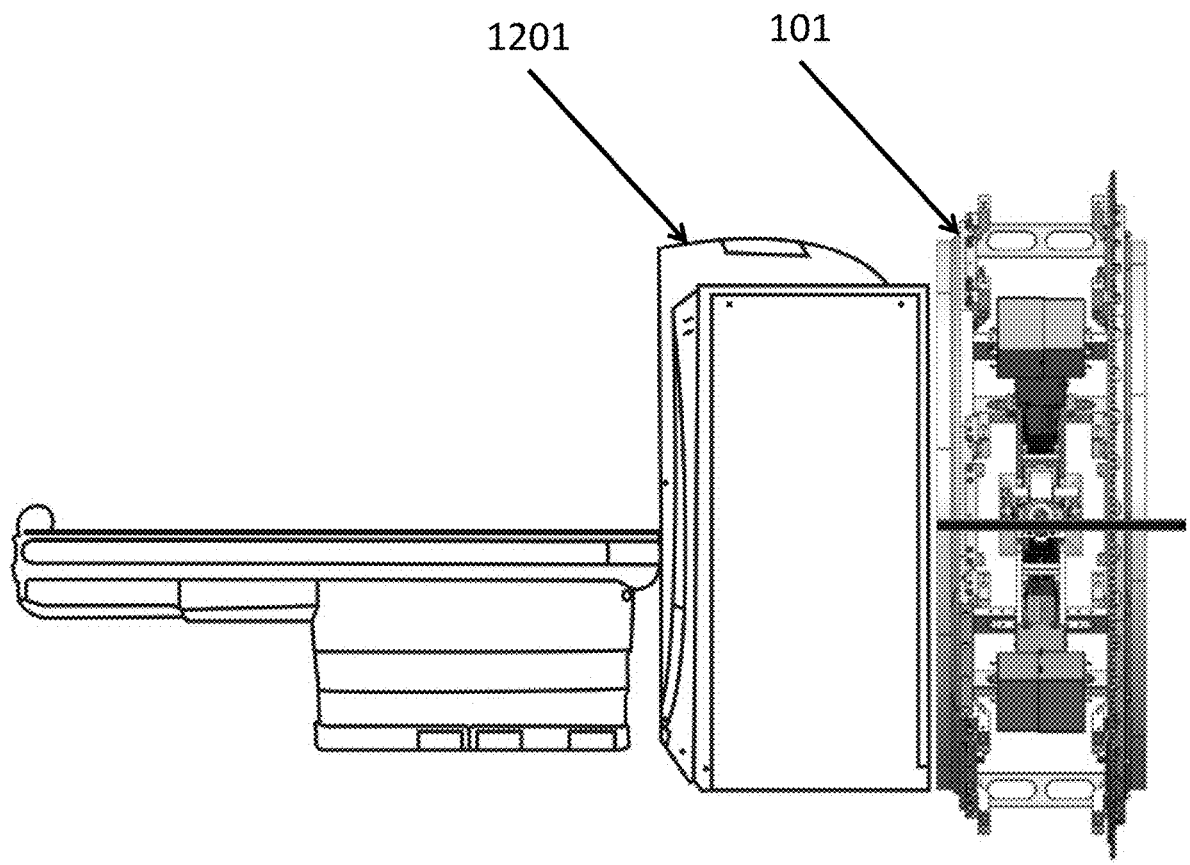
FIG. 13 is a simplified illustration of an exemplary radiation therapy device placed adjacent to a CT scanner in accordance with certain aspects of the present disclosure.

While the CT and RT systems in FIG. 13 are shown arranged so the couch first enters the CT, and then the RT device, it is contemplated that the arrangement could be reversed.

In typical embodiments of the combined CT/RT system, the CT system and RT system are generally lined up with one another so that a couch can translate a patient in one direction to move from one system to the other. For example, when the RT system includes a gantry having a bore (e.g., a ring gantry), the bores of the CT and RT system are generally aligned. In the case where the overall height of the RT system is greater than the height of the CT system, this may be accomplished by raising the CT system on a platform or by lowering the RT system through use of a pit in the floor of the treatment room (see illustration in FIG. 15 of an RT system 101 viewed from the end, showing the system's bore and a pit 1504 in the floor; the pit can also be seen in FIG. 14).

The combined CT/RT system may utilize a couch configured to position the patient both for imaging and for radiation therapy by translating the patient between the diagnostic quality CT scanner and the radiation therapy device.

A couch may be specially designed for the combined CT/RT system. In one implementation, the couch would be designed to move up and down, and to translate through the bore(s) of the system, but may be configured to not rotate, as discussed above. Alternatively, an off-the-shelf CT simulator couch may be used and positioned as close as possible to the CT/RT system so it can extend through both isocenters. In another implementation, an off-the-shelf PET/CT scanner couch can be used, as it is designed for use in a multiple iso-center system. When the term "off-the-shelf" system is used herein, it refers to a system that can be purchased in a configuration ready to be used, or used with only minor modifications.

The principles discussed above with regard to the contemplated radiotherapy delivery systems apply to the combined CT/RT systems of the present disclosure as well. For example, the combined system may be configured to deliver only co-planar radiation therapy. In an exemplary embodiment, the radiation beam source may only travel within a plane (e.g., on a ring gantry), the RT device may not be cantilevered, and the RT/CT couch may not be configured to rotate.

The combined CT/RT system has the ability to acquire diagnostic-quality CT images of a patient on the treatment couch, just prior to radiation therapy, which can provide a number of benefits. For one, the patient will be positioned in exactly the same manner for pre-treatment imaging and for the treatment itself, thereby reducing treatment errors that may occur when a patient's body is positioned or supported in a different way between imaging and treatment.

Other benefits to the combined CT/RT system are realized through use of its control systems and associated software. For example, the system can be configured to reoptimize treatment plans and perform on-table adaptive therapy based on its diagnostic-quality CT imaging.

In one implementation of this functionality, the treatment couch can move the patient into position for CT imaging. Because the imaging received is diagnostic quality, the system can effectively apply deformable image registration to morph the original treatment plan onto the current CT. The system can then allow for autocontoring of the tissues and targets that were segmented in the original plan onto the current CT scan. The CT numbers on the current scan can be converted to electron densities to compute an accurate dose delivery prediction before treating the patient. The quality of the dose distribution for the current plan may then be assessed and, if the plan is suboptimal (e.g., dose to the tumor/target too low or dose to critical structures too high), the treatment plan can be reoptimized to improve the dose distribution on the spot. The couch may then move the patient toward the RT isocenter for treatment. In this way, the system is capable of adapting to conditions relating to the patient or patient setup that may have changed since the time the original treatment plan was created and to deliver an improved plan. Such adaptive treatment/reoptimization can significantly improve dose distributions and patient outcomes. In one implementation, the system can be configured to utilize diagnostic-quality CT images to reoptimize a treatment plan, and may be configured to do so just prior to treatment, while the patient is on the couch.

Functionalities of the control systems and software can thus include, but are not limited to, CT image acquisition, deformable image registration, automatic tissue segmentation/contouring, dose computation, treatment plan optimization and radiation therapy delivery.

Figure 14:
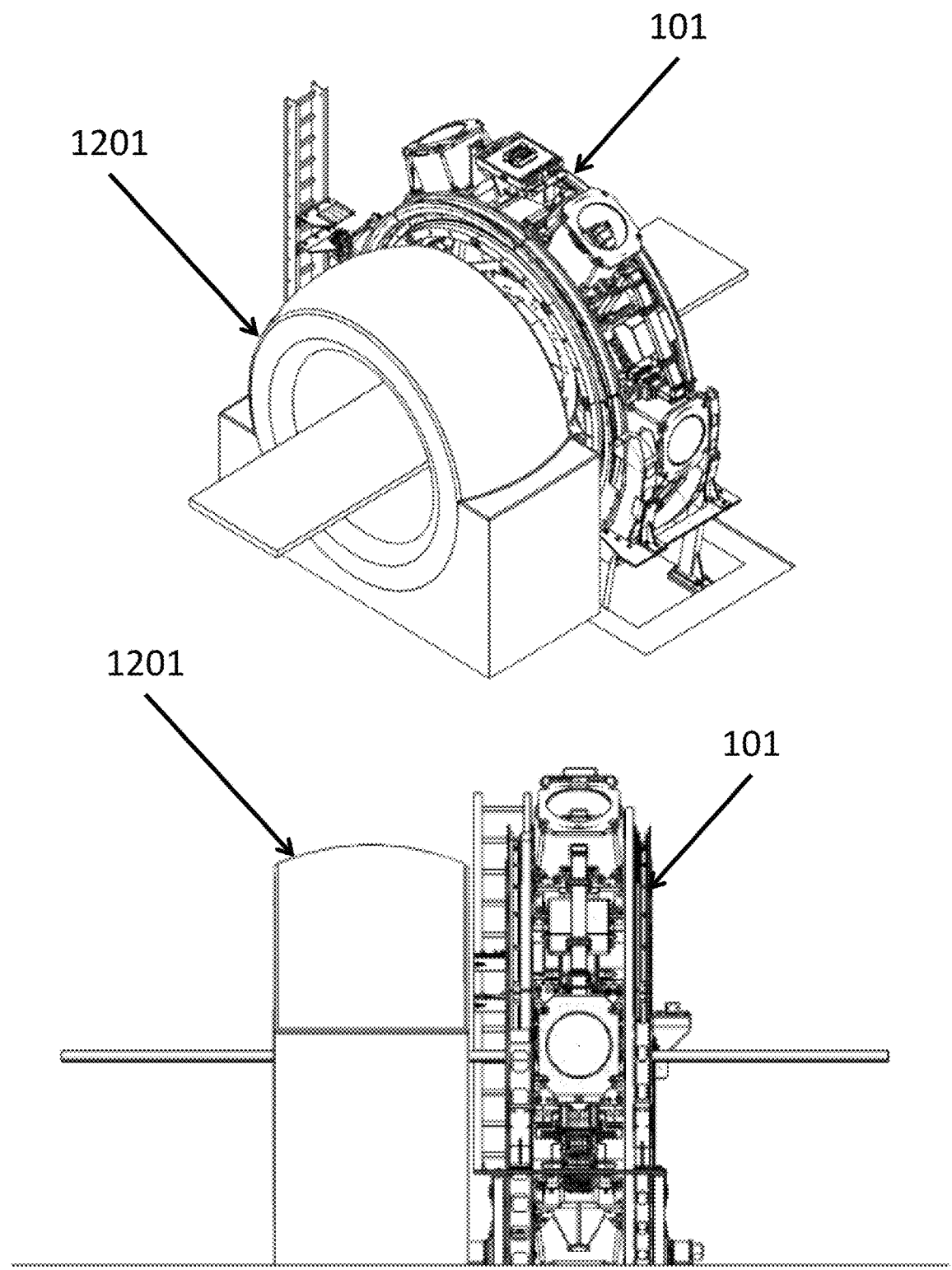
FIG. 14 is a simplified illustration of exemplary arrangements for a combination CT/RT system in accordance with certain aspects of the present disclosure.
Figure 15:
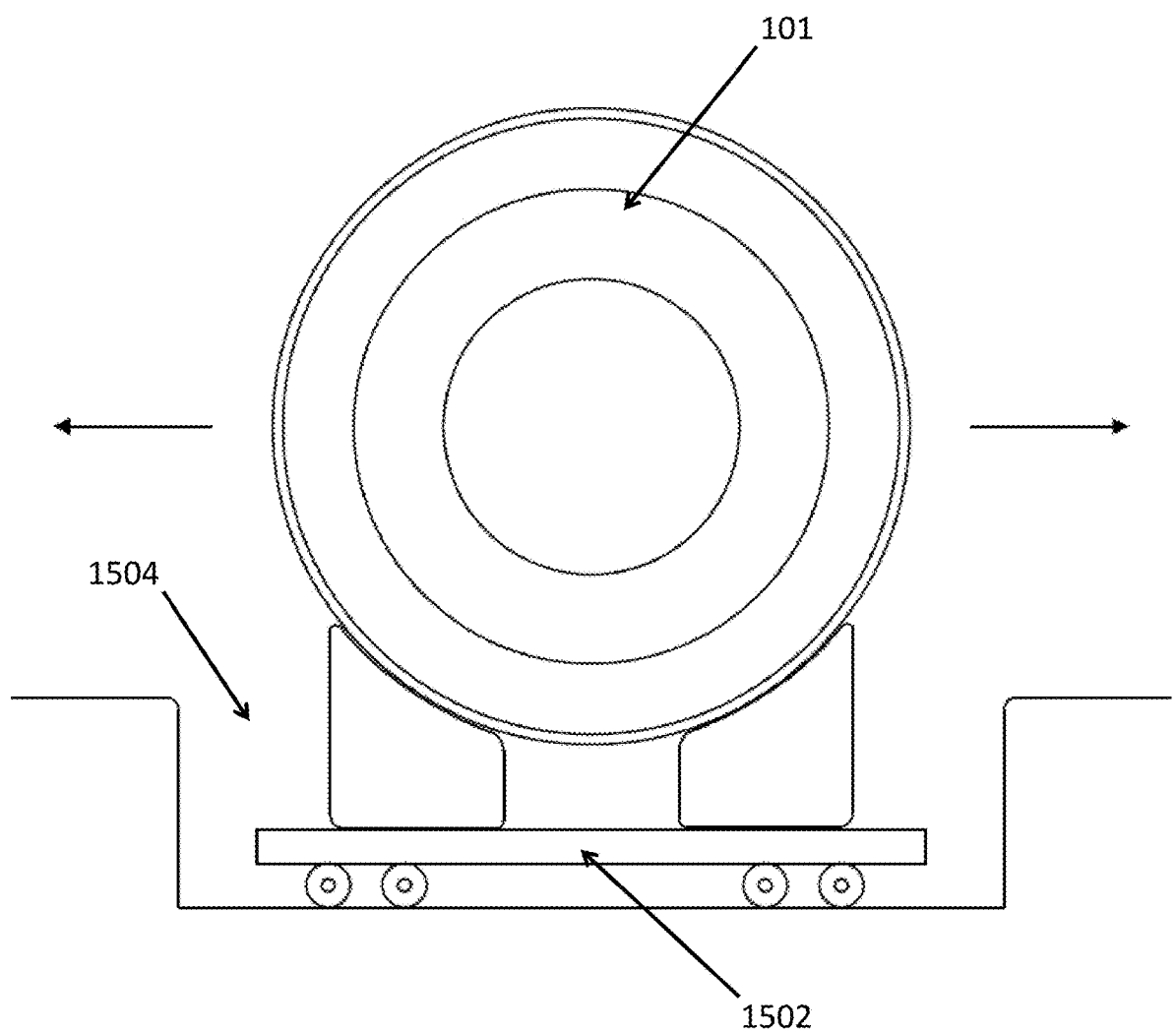
FIG. 15 is a simplified illustration of an exemplary radiation therapy device configured to move laterally in accordance with certain aspects of the present disclosure.

FIG. 14 includes additional views of an exemplary arrangement for a combination CT/RT system. RF shielding may be included in certain embodiments of the CT/RT systems disclosed herein. As an example, when the radiation therapy beam source is a linear accelerator, RF radiation from various linac components may interfere with devices in the room, or in the patient (such as pacemakers, ICDs, etc.). One manner for reducing interference is to utilize RF shielding in containers for linac components 1102. Examples of such containers can be seen in FIG. 14 and are discussed in detail in U.S. Pat. Nos. 8,836,332 and 9,446,263 to the current assignee, which are incorporated herein by reference.

Embodiments of the combined CT/RT systems may also include radiation shielding for components of the CT scanner, to prevent damage to scanner components caused by the scatter of megavoltage radiation from the radiation therapy beam source. One implementation may utilize a shield between the diagnostic-quality CT scanner and the radiation therapy device. Another implementation may form fit and cover or replace the outer shroud of the CT scanner facing toward the radiation therapy unit with a high atomic number material to absorb or scatter radiation away from the unprotected components of the X-Ray CT scanner. For example, the shielding material may be a few centimeters of lead or a single centimeter of tungsten.

Figure 16:
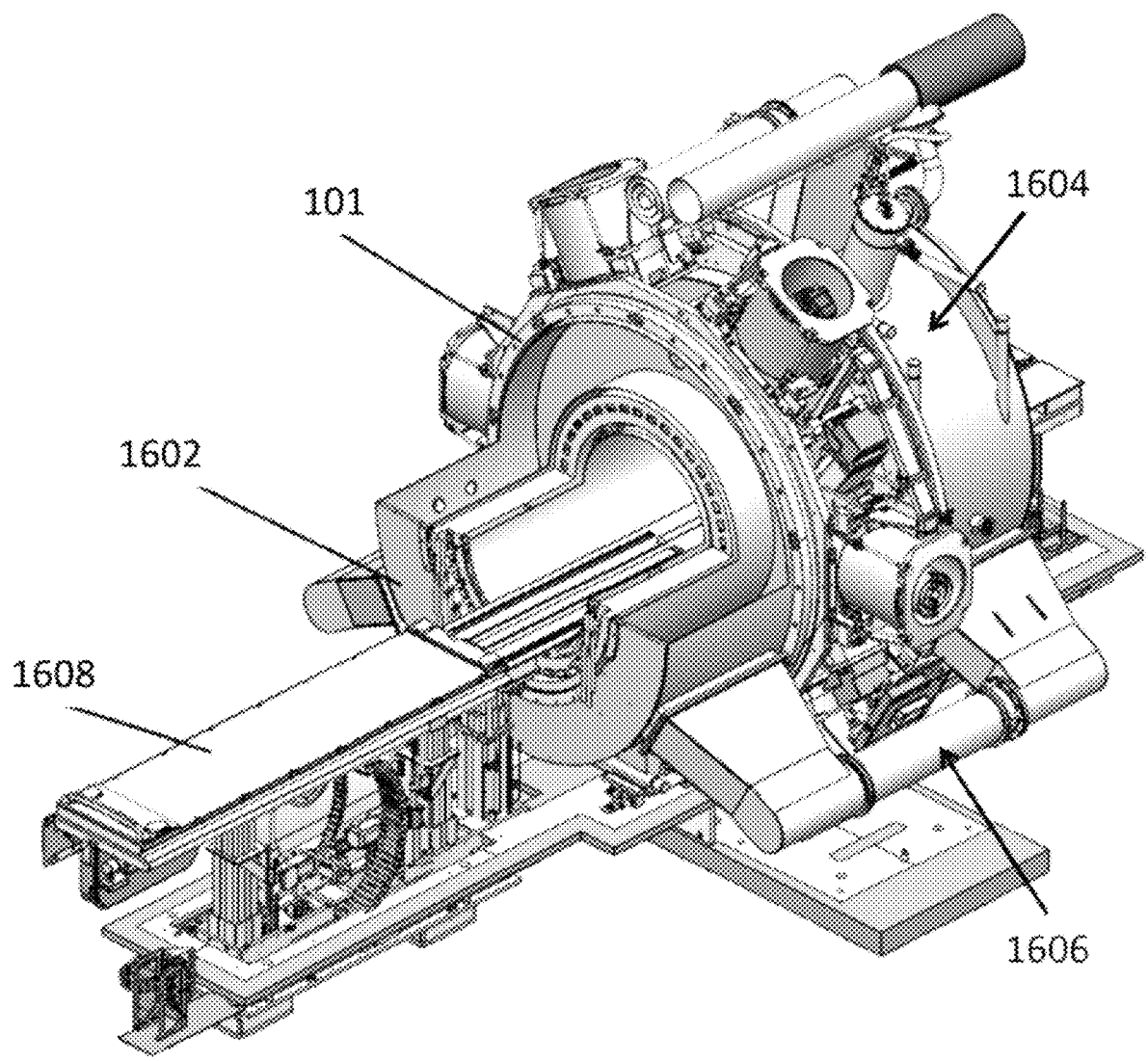
FIG. 16 is a simplified illustration of an RT system combined with an exemplary split MRI design, and versatile base plate(s) in accordance with certain aspects of the present disclosure.

In certain embodiments, the chosen treatment couch may have limited degrees of freedom. For example, the couch may only be able to translate up and down, and in and out of the bore (as is the case with typical off-the-shelf CT systems). Such a lack of lateral movement may cause issues with positioning a patient for radiation treatment if the target is located lateral from the patient's longitudinal axis or away from the midsagittal plane. It is contemplated that a number of designs can overcome this limitation. For example, an off-the-shelf CT couch can be mounted on a platform capable of lateral movement. Alternatively, a couch could be altered or redesigned to include the additional degree of freedom. In the embodiment depicted in FIG. 15, the radiation therapy device 101 (depicted here inside of optional pit 1504) may be configured to itself be shifted to move laterally with respect to the couch and the patient located within its bore. In one embodiment, the gantry may be configured to be translated orthogonally to couch motion over a range of at least 8 cm to facilitate the positioning of the radiation therapy isocenter in the patient before treatment The radiation therapy devices described herein may also be configured for use with an MRI, as described in a number of additional patents and applications assigned to the assignee of the present disclosure (e.g., U.S. Pat. No. 9,446, 263). FIG. 16 shows an example of such a configuration, utilizing a split MRI design with magnet halves 1602 and 1604 that surround radiation therapy device 101 and are connected by buttresses 1606.

The system may be designed to be installed with either MRI guidance or X-Ray CT guidance and may also be designed to facilitate conversion between the different types of guidance through a versatile base plate or multiple versatile base plates (see, e.g., FIG. 16). The base plate(s) cover at least a portion of the area under the system sufficient for rigidly mounting and aligning it. As one example, the base plate(s) may be designed with a number of drill patterns to accept, for example, 1) the RT device, 2) a CT scanner or an MRI, and 3) a CT couch, PET/CT couch or MRI couch. In this matter, a system could be converted from CT guidance to MRI guidance without removing or disturbing the radiation therapy device itself.

One or more aspects or features of the subject matter described herein, for example, the control systems for multileaf collimators, can be realized in digital electronic circuitry, integrated circuitry, specially designed application specific integrated circuits (ASIC s), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Aspects of the subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention (s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A computer program product comprising a non-transitory, machine-readable medium storing instructions which, when executed by at least one programmable processor, cause the at least one programmable processor to perform operations comprising:
   receiving a treatment plan for the delivery of radiation therapy;
   receiving diagnostic-quality CT images from a diagnostic-quality CT scanner;
   morphing the treatment plan onto the diagnostic-quality CT images by applying deformable image registration to the treatment plan;
   assessing a quality of dose distribution for the treatment plan;
   re-optimizing the treatment plan when the quality of dose distribution is determined to be suboptimal; and
   determining a dose delivery prediction by converting diagnostic-quality CT numbers in the diagnostic-quality CT images to electron densities.

2. The computer program product of claim 1, the operations further comprising:
   controlling a patient couch to place the patient at a position for diagnostic-quality CT imaging; and
   controlling the patient couch to place the patient at the radiation therapy isocenter after receiving the diagnostic-quality CT images.

3. The computer program product of claim 1, the operations further comprising:
   autocontouring tissues and/or targets that were segmented in the treatment plan onto the diagnostic-quality CT images.

4. The computer program product of claim 1, the operations further comprising:
   controlling a patient couch to place the patient at a position for diagnostic-quality CT imaging; and
   performing the reoptimizing prior to delivery of radiation therapy.

5. A system comprising:
   a diagnostic-quality CT scanner for imaging a patient, the diagnostic-quality CT scanner having an imaging isocenter;
   a radiation therapy device positioned adjacent the diagnostic-quality CT scanner, the radiation therapy device including a gantry carrying a radiation therapy beam source and having a radiation therapy isocenter separate from the imaging isocenter of the diagnostic-quality CT scanner;
   a patient couch configured to position the patient for imaging and for radiation therapy by translating the patient between the diagnostic-quality CT scanner and the radiation therapy device; and
   a non-transitory, machine-readable medium storing instructions which, when executed by at least one programmable processor, cause the at least one programmable processor to perform operations comprising:
      receiving a treatment plan for the delivery of radiation therapy;
      receiving diagnostic-quality CT images from the diagnostic-quality CT scanner;
      morphing the treatment plan onto the diagnostic-quality CT images by applying deformable image registration to the treatment plan;
      assessing a quality of dose distribution for the treatment plan;
      reoptimizing the treatment plan when the quality of dose distribution is determined to be suboptimal; and
      determining a dose delivery prediction by converting diagnostic-quality CT numbers in the diagnostic-quality CT images to electron densities.

6. The system of claim 5, the operations further comprising:
   controlling the patient couch to place the patient at a position for diagnostic-quality CT imaging; and
   controlling the patient couch to place the patient at the radiation therapy isocenter after receiving the diagnostic-quality CT images.

7. The system of claim 5, the operations further comprising:
   autocontouring tissues and/or targets that were segmented in the treatment plan onto the diagnostic-quality CT images.

8. The system of claim 5, the operations further comprising:
   controlling the patient couch to place the patient at a position for diagnostic-quality CT imaging; and
   performing the reoptimizing prior to delivery of radiation therapy.

* * * * *